US007442682B2

(12) United States Patent
Kitaura et al.

(10) Patent No.: US 7,442,682 B2
(45) Date of Patent: Oct. 28, 2008

(54) TRANSEPITHELIAL DELIVERY OF PEPTIDES WITH INCRETIN HORMONE ACTIVITIES

(75) Inventors: Chieko Kitaura, Osaka (JP); Kenjiro Minomi, Osaka (JP); Katsuyuki Okubo, Osaka (JP); Keisaku Okada, Osaka (JP); Natsuko Kagehisa, Osaka (JP); Masashi Kamiyama, Osaka (JP); Zheng Hou, Vista, CA (US); Jian Liu, San Diego, CA (US); Yucheng Song, Oceanside, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 229 days.

(21) Appl. No.: 11/219,145

(22) Filed: Sep. 2, 2005

(65) Prior Publication Data
US 2006/0084604 A1  Apr. 20, 2006

Related U.S. Application Data

(60) Provisional application No. 60/620,001, filed on Oct. 19, 2004.

(51) Int. Cl.
| | |
|---|---|
| *A61K 9/00* | (2006.01) |
| *A61K 9/06* | (2006.01) |
| *A61K 38/22* | (2006.01) |
| *A61K 38/28* | (2006.01) |
| *A61K 47/42* | (2006.01) |
| *C07K 14/00* | (2006.01) |

(52) U.S. Cl. ................ 514/3; 514/2; 514/12; 530/300; 530/303; 530/308; 530/324; 564/236

(58) Field of Classification Search ................ None
See application file for complete search history.

(56) References Cited

U.S. PATENT DOCUMENTS

| | | | | |
|---|---|---|---|---|
| 5,424,286 | A | | 6/1995 | Eng |
| 5,766,620 | A | * | 6/1998 | Heiber et al. ............... 424/436 |
| 5,882,675 | A | | 3/1999 | Ninomiya et al. |
| 6,146,656 | A | | 11/2000 | Hori et al. |
| 6,669,951 | B2 | | 12/2003 | Rothbard et al. |
| 6,703,359 | B1 | | 3/2004 | Young et al. |
| 7,060,708 | B2 | * | 6/2006 | Piccariello et al. .......... 514/282 |
| 2003/0032593 | A1 | | 2/2003 | Wender et al. |

FOREIGN PATENT DOCUMENTS

| | | |
|---|---|---|
| WO | WO 03/049772 | 6/2003 |
| WO | WO 03/072195 | 9/2003 |
| WO | WO 2005/000222 | 1/2005 |
| WO | WO 2005/117584 | 12/2005 |

OTHER PUBLICATIONS

Pi-interaction from www.chemsoc.org/ExemplarChem/entries/2004/warwick-robinson/Pi.htm.*
Boger RH and Bode-Boger SM, The Clinical Pharmacology of L-Arginine, Annu. Rev. Pharmacol. Toxicol., 2001, 41: 79-99.*
Daibetes, Heart Disease and Stroke, from www. diabetes.org/heart-disease-stroke.jsp.*
Drucker, "Enhancing Incretin Action for the Treatment of Type 2 Diabetes," *Diabetes Care*, vol. 26, No. 10, pp. 2929-2940, Oct. 2003.
Kim, et al. "Development and Characterization of a Glucagon-Like Peptide 1-Albumin Conjugate," *Diabetes*, vol. 52, pp. 751-759, Mar. 2003.
Knudsen, "Glucagon-Like Peptide-1: The Basis of a New Class of Treatment for Type 2 Diabetes," *Journal of Medicinal Chemistry*, vol. 47(17): pp. 4128-4134, Aug. 12, 2004.
Kolterman, et al. "Synthetic Exendin-4 (Exenatide) Significantly Reduces Postprandial and Fasting Plasma Glucose in Subjects with Type 2 Diabetes," *The Journal of Clinical Endocrinology & Metabolism*, vol. 88, No. 7, pp. 3082-3089, 2003.
Nielsen, et al. "Pharmacology of Exenatide (Synthetic Exendin-4) for the Treatment of Type 2 Diabetes," *Current Opinion in Investigational Drugs*, vol. 4, No. 4, pp. 401-405, Apr. 2003.
Orskov, et al. "Pharmacokinetic, Insulinotropic, and Glucagonostatic Properties of GLP-1 [7-36 amide] After Subcutaneous Injection in Healthy Volunteers. Dose-Response-Relationships," *Diabetologia*, vol. 38, No. 6, pp. 720-235, Jun. 1995 (Abstract only).
Stoffers, et al. "Neonatal Exendin-4 Prevents the Development of Diabetes in the Intrauterine Growth Retarded Rat," *Diabetes*, vol. 52, pp. 734-740, Mar. 2003.
Thorkildsen, et al. "Glucagon-Like Peptide 1 Receptor Agonist ZP10A Increases Insulin mRNA Expression and Prevents Diabetic Progression in *db/db* Mice," *The Journal of Pharmacology and Experimental Therapeutics*, vol. 307, No. 2, pp. 490-496, 2003.
Zander, et al. Effect of 6-week Course of Glucagon-Like Peptide4 1 on Glycaemic Control, Insulin Sensitivity, and β-cell Function in Type 2 Diabetes: A Parallel-Group Study, *The Lancet*, vol. 359, pp. 824-830, Mar. 9, 2002.
"Liraglutide." Article downloaded from the glucagon.com website, dated Aug. 30, 2004, 3 pages.
Review article by Nuria Morral in *Trends in Endocrinology and Metabolism*, May 2003, regarding Newer Approaches to the Treatment of Type 2 Diabetes.
Rothbard, et al. "Conjugation of Arginine Oligomers to Cyclosporin A Facilitates Topical Delivery and Inhibition of Inflammation," *Nature Medicine*, vol. 6, No. 11, pp. 1253-1257, Nov. 2000.

\* cited by examiner

*Primary Examiner*—Anish Gupta
*Assistant Examiner*—Julie Ha
(74) *Attorney, Agent, or Firm*—Knobbe, Martens, Olson & Bear, LLP

(57) ABSTRACT

Compositions and methods are disclosed for the treatment of diabetes and related diseases using peptides with incretin hormone activity. Preferably, the peptide with incretin hormone activity is GLP-1, exendin or an analog of GLP-1 or exendin. The peptides with incretin hormone activity are administered transepithelially using a transepithelial carrier peptide. The transepithelial peptide contains sufficient amino, guanidine or amidino groups to stimulate transepithelial delivery. In some embodiments, the transepithelial carrier and the peptide with incretin hormone activity are embedded in a pressure sensitive adhesive layer of a plaster or patch.

29 Claims, 4 Drawing Sheets

TRANSEPITHELIAL DELIVERY OF PEPTIDES WITH INCRETIN HORMONE ACTIVITIES

RELATED APPLICATIONS

This application claims priority to U.S. Provisional Application No. 60/620,001 filed Oct. 19, 2004 which is incorporated herein by reference.

BACKGROUND OF THE INVENTION

1. Field of the Invention

Embodiments of the invention relate to compositions and methods for transepithelial delivery of peptides with incretin hormone activity for the treatment of chronic disease conditions, particularly diabetes mellitus. Oligopeptides are used to facilitate topical delivery.

2. Description of the Related Art

Diabetes mellitus is a group of metabolic diseases characterized by elevated blood sugar levels (hyperglycermia). Hyperglycermia is a result of absolute or relative insufficiency of insulin secretion or resistance to insulin action or both. The majority of diabetes cases fall into two categories: type 1 diabetes and type 2 diabetes. Type 2 diabetes is the most common form of diabetes, accounting for 90% of cases. An estimated 16 million Americans have type 2 diabetes. Type 2 diabetes is usually caused by resistance to insulin action in the setting of inadequate compensatory insulin secretory response. (c.f. Jay S. Skyler "Diabetes Mellitus: Pathogenesis and Treatment Strategies" Journal of Medicinal Chemistry, 2004, vol. 47, 4113-4117.)

Insulin is a key player in the control of carbohydrate and lipid metabolism. When glucose is liberated from dietary carbohydrate and absorbed into the blood, elevated concentrations of blood glucose stimulate release of insulin. Insulin facilitates entry of glucose into muscle, adipose and several other tissues. Insulin also stimulates the liver to store glucose in the form of glycogen. As blood glucose concentrations fall, insulin secretion ceases. In the absence of insulin, the cells in the body will switch to using alternative fuels like fatty acids for energy, and subsequently, enzymes will break down the glycogen in the liver.

Insulin also has important effects on lipid metabolism. Insulin promotes synthesis of fatty acids in the liver. When the liver is saturated with glycogen, any additional glucose taken up by hepatocytes is shunted into pathways leading to synthesis of fatty acids, which are exported from the liver as lipoproteins. Insulin also inhibits breakdown of fat in adipose tissue. From a whole body perspective, insulin has a fat-sparing effect. Not only does it drive most cells to preferentially oxidize carbohydrates instead of fatty acids for energy, insulin indirectly stimulates accumulation of fat in adipose tissue.

Because of the important role insulin plays in the control of carbohydrate and lipid metabolism, derangements in insulin secretion and action have widespread and devastating effects on many organs and tissues. Diabetes mellitus, the most important metabolic disease of man, is an insulin deficiency state. Type 1 or insulin-dependent diabetes mellitus is the result of an immune-mediated destruction of pancreatic islet β-cells with consequent insulin deficiency and the need to replace insulin. Type 2 or non-insulin-dependent diabetes mellitus is a syndrome of insulin resistance, in which target tissues fail to respond appropriately to insulin. Diabetes patients suffer the pervasive metabolic derangements that include altered metabolism of carbohydrates, fats and proteins. Over time, metabolic disruption may lead to long-term damage, dysfunction and failure of various organs, especially the eyes, kidneys, nerves, heart and blood vessels.

Current pharmacologic agents used to treat type 2 diabetes include insulin, biguanides, sulfonylureas and thiazolidinediones. Because of the natural progression of type 2 diabetes, most diabetes patients eventually require insulin therapy. The major drawbacks of these drugs include low blood glucose (hypoglycemia), weight gain and edema. In addition, none of these compounds offer the potential to preserve the function of insulin-producing β-cells in the pancreas.

Incretin hormones are hormones that cause an increase in the amount of insulin released when glucose levels are normal or, more particularly, when they are elevated. These incretin hormones have other actions beyond the initial incretin action defined by insulin secretion. They also have actions to reduce glucagon production and delay gastric emptying. They may also have actions to improve insulin sensitivity, and they may increase islet cell neogenesis, namely the formation of new islets. Incretin hormones augment insulin response when glucose is absorbed through the gut. There are two known incretin hormones in humans: glucose-dependent insulinotropic polypeptide (GIP) and glucagon-like peptide-1 (GLP-1). The therapeutic use of incretin hormones in treating conditions including diabetes, obesity, cardiovascular diseases and Alzheimer's disease is currently an area of intense research activity.

Glucose-dependent insulinotropic polypeptide (GIP) is a gastrointestinal peptide of 42 amino acids. GIP is released from duodenal endocrine K cells after absorption of glucose or fat. Glucagon-like peptide-1 (GLP-1) is synthesized in the L-cells of the lower intestinal tract in response to the presence of nutrients in the distal small intestine. Both GIP and GLP-1 potentiate glucose-induced insulin secretion from the pancreatic β-cells.

The important effects of the GIP and GLP-1 on carbohydrate and lipid metabolism have been demonstrated through experiments involving deleting the genes of their receptors. Knockout of the GIP receptor is associated with significant glucose intolerance. It has also been found that mice lacking GIP receptors are protected from both obesity and insulin resistance when being fed with a high-fat diet. Mice without GLP-1 receptors are glucose intolerant and exhibit fasting hyperglycemia.

GLP-1 is one of the most potent insulinotropic substances with half-maximal effective concentration on β-cells at 10 pmole/l. The insulinotropic effect of GLP-1 is strictly glucose dependent. GLP-1 stimulates all steps of insulin biosynthesis as well as insulin gene transcription, thereby providing continued and augmented supplies of insulin for secretion. GLP-1 has trophic effects on β-cells. It stimulates β-cell proliferation and enhances the differentiation of new β-cells from progenitor cells in the pancreatic duct epithelium. GLP-1 also inhibits both cytokine and fatty acid-induced apoptosis in β-cells. Patients with type 2 diabetes mellitus have significantly impaired GLP-1 secretion and impaired responsiveness of β cells to GIP. However, near normal insulin responses are restored in type 2 diabetes patients after GLP-1 injection. Therefore, GLP-1 represents an attractive antidiabetic agent.

Exendin peptides were isolated from the salivary glands of the lizard *Heloderma* species. They were so named for the reason that they were isolated from an exocrine gland and were subsequently shown to have endocrine actions. Exendin-3 was isolated from *Heloderma horridum* and exendin-4 was isolated from *Heloderma suspectum*. These two peptides share an identical sequence except for substitutions in residues 2 and 3 from the amino terminus, and both peptides can stimulate cAMP activity in dispersed pancreatic acinar cells. Exendin-4 is a potent agonist for the mammalian GLP-1 receptor. Exendin-4 is much more potent than native GLP-1 for the treatment of diabetes, largely due to its resistance to the aminopeptidase dipeptidyl peptidase IV (DPP-IV) mediated inactivation. In contrast to GLP-1 which contains an alanine at position 2, exendin-4 has a position 2 glycine; hence it is not a substrate for DPP-IV and has a much longer t1/2 in vivo.

In a study in which patients received infusion of natural GLP-1 via MiniMed insulin pumps for 6 weeks, it was demonstrated that GLP-1 can rapidly lower fasting blood glucose by 4-5 mM, mainly within the first week of treatment. (Zander, M.; Madsbad, S.; Madsen, J. L.; Holst, J. J. "Effect of 6-Week Course of Glucagon-Like Peptide 1 on Glycaemic Control, Insulin Sensitivity, and Beta-Cell Function in Type 2 Diabetes: A Parallel-Group Study". *Lancet* 2002, 359, 824-830.) The potent glucose-lowering properties of GLP-1 and its analogs, including exendin-4 (exenatide, AC2993) from Lilly and Amylin (Stoffers, D. A.; Desai, B. M.; DeLeon, D. D.; Simmons, R. A. "Neonatal Exendin-4 Prevents the Development of Diabetes in the Intrauterine Growth Retarded Rat." *Diabetes* 2003, 52, 734-740.), liraglutide (γ-L-glutamoyl(N-R-hexadecanoyl))-Lys26,Arg34-GLP-1(7-37), NN2211) from Novo Nordisk (Elbrond, B.; Jakobsen, G.; Larsen, S.; Agerso, H.; Jensen, L. B.; Rolan, P.; Sturis, J.; Hatorp, V.; Zdravkovic, M. "Pharmacokinetics, Pharmacodynamics, Safety, and Tolerability of a Single-Dose of NN2211, a Long-Acting Glucagon-Like Peptide 1 Derivative, in Healthy Male Subjects". *Diabetes Care* 2002, 25, 1398-1404.), CJC-1131 (D-Ala8Lys37[2-[2-[2-maleimidopropionamido(ethoxy) ethoxy]acetamide-GLP-1(7-37)) from Conjuchem (Kim, J. G.; Baggio, L. L.; Bridon, D. P.; Castaigne, J. P.; Robitaille, M. F.; Jette, L.; Benquet, C.; Drucker, D. J. "Development and Characterization of a Glucagon-Like Peptide 1-Albumin Conjugates The Ability To Activate the Glucagon-Like Peptide 1 Receptor in Vivo". *Diabetes* 2003, 52, 751-759.), ZP-10A from Zealand and Aventis (Petersen, J. S.; Thorkildsen, C.; Lundgren, K.; Neve, S. "ZP10: A New GLP-1 Agonist That Prevents Diabetes Progression and Increases Insulin mRNA Expression in Db/Db Mice". *Diabetologia* 2002, 45, A147.) and BIM-51077 from Ipsen (Dong, J. Z.; Shen, Y.; Zhang, J.; Taylor, J. E.; Woon, C.; Morgan, B.; Skinner, S.; Cawthorne, M.; Culler, M.; Moreau, J. "Design and Synthesis of a Novel GLP-1 Analog, BIM-51077, Which Has Significantly Improved in Vivo Activity". *Biopolymers* 2003, 71, 391.), have prompted consideration of its use for the treatment of patients with Type 2 diabetes. The above is summarized in Table 1 below.

TABLE 1

Proprietary GLP-1 receptor agonists

| GLP agonist | Chemical name | Developer | Reference |
|---|---|---|---|
| Exenatide, AC2993 | Exendin-4, see SEQ ID NO: 6 | Lilly & Amylin | Stoffers, et al. ((2003) Diabetes 52: 734 |
| Liraglutide | γ-L-glutamoyl (N-R-hexadecanoyl)-Lys26, Arg34-GLP-1(7-37), NN2211 | Novo Nordisk | Elrond, et al. (2002) Diabetes Care 25: 1398 |
| CJC-1131 | D-Ala, 8Lys37[2-[2-[2-maleimido-propionamido(ethoxy)-ethoxy]acetamide-GLP-1(7-37) | Conjuchem | Kim, et al. (2003) Diabetes 52: 751 |
| ZP10A | See SEQ ID NO: 35 | Zealand & Aventis | Petersen, et al. (2002) Diabetologia2002, 45: A147 |
| BIM-51077 | | Ipsen | Dong, et al. (2003) Biopolymers 71, 391 |

Drug delivery is the biggest challenge for the development of GLP-1 and its analogs into therapeutics. The compounds mentioned above are all peptides and have to be injected. Transit nausea and vomiting are the major side effects of this class of compounds and are associated with peak concentrations introduced by injection. These side effects limited the dosage of GLP-1 in human studies (Drucker, Daniel J. "Enhancing Incretin Action for the Treatment of Type 2 Diabetes" (October 2003) Diabetes Care vol. 26 (10): 2929-2940). Likewise, Nielsen, et al. report that the optimal glucose-lowering dose range for exenatide (synthetic exendin-4) is 0.05 to 0.2 μg/kg, but that nausea and vomiting are dose-limiting (Nielson, et al. (April 2003) "Pharmacology of exenatide (synthetic exendin-4) for the treatment of type 2 diabetes" Current Opinion in Investigational Drugs vol. 4 (4): 401-405). A need exists to provide a therapeutic dose of a diabetic drug treatment such as GLP-1 or an analog thereof, while minimizing unwanted side effects.

Drug delivery through the transdermal pathway offers clear advantages. First, transdermal delivery potentially improves patient compliance compared with oral delivery. Smaller doses may be used for the same drug, helping to minimize side effects such as nausea. Second, the problem of first-pass metabolism is avoided, as well as the peaks and valleys created by oral delivery and GI tract absorption. There are no restrictions around the time that the drug should be administered or whether the patient may eat afterward. In particular, multi-day patch delivery offers ease of use and is convenient, without the requirement to remember to take a medicine at a specific time. A final benefit of transdermal delivery versus oral or injection is that dosage may be stopped abruptly by simply removing the patch if adverse side effects are experienced.

As the largest organ in the human body, one of the most important functions of the human skin is to provide a physicochemical barrier to defend the body from the ingression of toxic chemicals and microorganisms. At the most coarse level, human skin is made of three layers. Stratum corneum, located on the outer surface of the skin, is a non-living layer of keratin-filled cells surrounded by a lipid-rich extracellular matrix that provides the primary barrier to drug delivery into skin. The epidermis below is a viable tissue devoid of blood vessels. Just below the dermal-epidermal junction, the dermis contains capillary loops that can take up transdermally administered drugs for systemic distribution. For most molecules the stratum corneum is the rate-limiting barrier to drug delivery. There are essentially three pathways by which a molecule can traverse intact stratum corneum. In the transappendageal route, a drug molecule takes advantage of the pores of hair follicles or sweat ducts to bypass the barrier of stratum corneum. In the transcellular route, a drug molecule penetrates across the stratum corneum through a series of events that include partition between bilayer lipid and keratin-filled cells followed by diffusion through the hydrated keratin. The intercellular lipid route provides the principal pathway by which most small, uncharged molecules traverse stratum corneum by moving through the continuous lipid domains between the keratinocytes.

Despite the success of transdermal delivery technology, the number of drugs that can be administered through the transdermal route is very limited. All of the drugs presently administered across skin share three constraining characteristics: low molecular mass (<500 Da), high lipophilicity (oil soluble) and small required dose (up to milligrams). There are a number of emerging technologies on the horizon that aim at removing these limitations for transdermal drug delivery. One of these technologies is the use of peptide oligomers with cell-penetrating properties as transdermal carriers. Cell-penetrating peptides are short polycationic oligomers that can penetrate across cell membranes through a receptor independent, non-endosome mechanism, potentially through interacting and disrupting of the bilayer lipid of the cell membrane. The same mechanism also potentially accounts for the transdermal activities of these peptides. In a recent paper, Rothbard et al. (Rothbard, J. B.; Garlington, S.; Lin, Q.; Kirschberg, T.; Kreider, E.; McGrane, P. L.; Wender, P. A.; Khavari, P. A. "Conjugation of arginine oligomers to cyclosporine A facilitates topical delivery and inhibition of inflammation", Nature Medicine, 2000, 6, 1253-1257) conjugated a heptamer of arginine to cyclosporine A through a pH-sensitive linker to produce R7-CsA. In contrast to unmodified cyclosporine A, which failed to penetrate skin, topically applied R7-CsA was efficiently transported into cells of mouse and human skin. R7-CsA reached dermal T lymphocytes and inhibited cutaneous inflammation.

The present inventors have discovered transdermal delivery methods for administration of peptide drugs with incretin hormone activity, particularly GLP-1 or exendin-4. It has been demonstrated that near normal insulin responses could be restored in type 2 diabetes patients after GLP-1 injection. Therefore, GLP-1 and its more stable analog exendin-4 are attractive antidiabetic agents. These peptide drugs are useful in treating diabetes, obesity, cardiovascular diseases and Alzheimer's disease.

For the treatment of such chronic disorders, non-invasive and patient friendly drug delivery methods such as oral, nasal or transdermal are clearly more practical than injection or drug pump implantation. Of these, transdermal delivery has many advantages over oral or nasal delivery for the administration of GLP-1 or exendin-4. Orally delivered peptide/protein drugs are subjected to harsh conditions prior to absorption through the gastrointestinal tract. During absorption through the nasal mucosa considerable metabolism may occur. The present invention successfully conjugated exendin-4 with a known transdermal carrier arginine oligomer. Our biological data showed significant enhancement for the transdermal delivery of such conjugates as compared with exendin-4 alone.

SUMMARY OF THE INVENTION

Embodiments of the invention are directed to compositions for the treatment of diabetes which include a topical preparation including a peptide with incretin hormone activity and a transepithelial carrier, along with a skin contact base. In preferred embodiments, the concentration of the peptide with incretin hormone activity in the skin contact base is from 0.001% to 70%, and the concentration of the transepithelial carrier in the skin contact base is from 0.001% to 70%. Preferably, the transepithelial carrier includes sufficient amino, guanidine or amidino groups to increase the delivery of the peptide with incretin hormone activity across intact animal epithelial tissue layers compared to delivery of the peptide in the absence of the transepithelial carrier.

In preferred embodiments, the topical preparation is a conjugate having one of the following structures, V or VI:

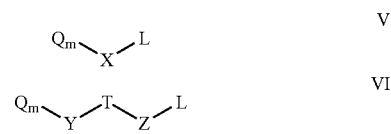

wherein:

Q includes the transepithelial carrier;

L includes the peptide;

X is a linkage formed between a functional group on the peptide and a functional group on the carrier;

Y is a linkage formed between a functional group on the linker and a functional group on the carrier;

Z is a linkage formed between a functional group on the peptide and a functional group on the linker;

T is a small oligopeptide linker; and m is an integer from 1-5.

In preferred embodiments, structures V and VI are capable of degradation by hydrolysis or glutathione-assisted reduction to release the peptide with incretin hormone activity in its bioactive form. In preferred embodiments, X, Y and Z are independently selected from —S—S—, —C(=O)O—, —C(=O)S—, —C(=O)NH—, —C(=S)NH—, —OC(=O)NH—, —NHC(=O)NH—, —CA=N—, an acetal linkage, a semi-acetal linkage, —SONH—, and —SO$_2$NH—, wherein A is H, alkyl or aryl.

In some preferred embodiments, the peptide and the transepithelial carrier are associated through noncovalent interactions such as electrostatic interaction, hydrogen bonding, π-stacking interaction and van der Waal interaction.

In preferred embodiments, the transepithelial carrier includes a mixture of a monomeric peptide and dimeric forms thereof. Preferably, the transepithelial carrier includes 5 to 50 amino acids, wherein at least 3 amino acids are arginines or lysines or analogs thereof. Preferably, at least one amino acid in the transepithelial carrier is a D-amino acid. In some preferred embodiments, all of the amino acids in the transepithelial carrier are D-amino acids.

In preferred embodiments, the transepithelial carrier includes at least one cysteine amino acid residue. More preferably, the transepithelial carrier includes a peptide monomer, a homodimer thereof, or a mixture of the monomers and the homodimers bound to the peptide with incretin activity though a disulfide bond. In preferred embodiments, at least one amino acid in the transepithelial carrier is a D-amino acid. In some preferred embodiments, all of the amino acids in the transepithelial carrier are D-amino acids.

In preferred embodiments, the peptide with incretin activity includes at least one cysteine amino acid residue, wherein the at least one cysteine is introduced by addition or replacement, or is innately present in the peptide with incretin activity. Preferably, the cysteine amino acid residue is attached to the N-terminus or the C-terminus of the peptide with incretin activity, or the cysteine amino acid residue replaces one of the serine amino acid residues in the peptide with incretin activity.

In a preferred embodiment, the peptide with incretin activity includes the amino acid sequence:

```
                                           (SEQ ID NO: 6)
      HGEGTFTSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a preferred embodiment, the peptide with incretin activity includes the amino acid sequence:

```
                                           (SEQ ID NO: 33)
      HSDGTFITSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a preferred embodiment, the peptide with incretin activity includes the amino acid sequence:

```
HAEGTFTSDV SSYLEGOAAK EFIAWLVKGR        (SEQ ID NO: 7)
``` wherein the cysteine amino acid residue is attached to the N-terminus or the C-terminus of the amino acid sequence, or the cysteine amino acid residue replaces one of the serine amino acid residues in the amino acid sequence.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. In yet more preferred embodiments, the transepithelial carrier is a peptide monomer, a homo-dimer thereof, or a mixture of the monomers and the homodimers bound to the peptide with incretin activity through a disulfide bond. In yet more preferred embodiments, at least one amino acid in the transepithelial carrier is a D-amino acid. In a highly preferred embodiment, all of the amino acids in the transepithelial carrier are D-amino acids. Preferably, the cysteine amino acid residue is attached to the N-terminus or the C-terminus of the peptide with incretin activity, or the cysteine amino acid residue replaces one of the serine amino acid residues in the peptide with incretin activity.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. More preferably, the peptide with incretin activity includes the amino acid sequence:

```
                                           (SEQ ID NO: 6)
      HGEGTFTSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. Preferably, the peptide with incretin activity includes the amino acid sequence:

```
                                           (SEQ ID NO: 33)
      HSDGTFITSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. Preferably, the peptide with incretin activity includes the amino acid sequence:

```
HAEGTFTSDV SSYLEGOAAK EFIAWLVKGR        (SEQ ID NO: 7)
``` and the cysteine amino acid residue is attached to the N-terminus or the C-terminus of the amino acid sequence, or the cysteine amino acid residue replaces one of the serine amino acid residues in the amino acid sequence.

In some preferred embodiments, the transepithelial carrier includes at least one peptide which includes a guanidinium group having the following structure (I):

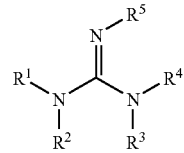

wherein R1, R2, R3, R4 and R5 are each individually selected from hydrogen, optionally substituted C1-C12 alkyl, optionally substituted C2-C12 alkenyl or optionally substituted C2-C12 alkynyl groups with the proviso that R1, R2, R3, R4 and R5 are not all hydrogen. More preferably, the alkyl, alkenyl or alkynyl groups are further substituted with other alkyl, alkenyl, alkynyl or aromatic groups, O, N, S, F, Cl, Br, P, and/or Si.

In some preferred embodiments, any one of the three nitrogen atoms in the guanidinium group participate in zero or one ring system with the proviso that no two nitrogen atoms in the guanidinium group participate in the same ring system.

In alternate preferred embodiments, any two of the three nitrogen atoms in the guanidinium group participate in the same ring system, and the remaining nitrogen atom in the guanidinium group participates in zero or one ring system, with the proviso that if the remaining nitrogen atom in the guanidinium group participates in the one ring system, the one-ring system is not fused to the ring system containing the two nitrogen atoms in the guanidinium group.

In alternate preferred embodiments, any two of the three nitrogen atoms in the guanidinium group participate in the same ring system, and the remaining nitrogen atom in the guanidinium group participates in a one ring system that is fused to the ring system containing the two nitrogen atoms in the guanidinium group.

In some preferred embodiments, the transepithelial carrier includes a peptide which contains a structure of the formula (II):

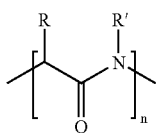

wherein R includes a guanidinium headgroup, R' is H, and n is an integer from 6 to 40. In preferred embodiments, one or more of the peptide bonds is replaced with at least one selected from —C(=O)NHO—, —C(=O)NHNH—, —S(=O)(=O)NR—, —P(=O)(—OR)NR'—, —CH2NR—, —CH2CH2C(=O)NR—, —C(=O)O—, —C(=S)NR—, —S(=O)(=O)CH2—, —SOCH2— and —CH2OC(=O)NR—.

In preferred embodiments, the transepithelial carrier includes a structure of formula (III):

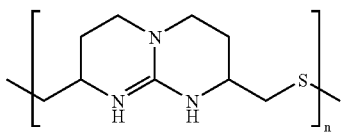

wherein n is an integer from 6 to 40.

In preferred embodments, the transepithelial carrier includes a peptoid of formula (IV):

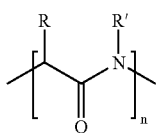

wherein either R or R' includes a guanidinium headgroup and n is the number of monomeric units in the peptoid. Preferably, the guanidinium headgroup is linked to the α carbon atom or α nitrogen atom through a linkage. More preferably, the linkage includes C, O, N, S, F, Cl, Br, P and/or Si atoms. More preferably, the linkage is 1-30 atoms in length.

In preferred embodiments, the peptide with incretin hormone activity is a therapeutic for a disease which is type 2 diabetes, obesity, cardiovascular disease and/or Alzheimer's disease. In preferred embodiments, the peptide with incretin hormone activity is glucagon-like peptide-1 (GLP-1), glucose-dependent insulinotropic polypeptide (GIP), exendin-4 or analogs thereof. In preferred embodiments, the peptide with incretin hormone activity is targeting glucagon-like peptide-1 receptors and glucose-dependent insulinotropic polypeptide receptors.

In preferred embodiments, the skin contact base is an ointment, a gel, an emulsion, a suspension, a cataplasm, a plaster, a lotion or a liniment. More preferably, the skin contact base is a plaster, which includes a pressure sensitive adhesive and a backing. Yet more preferably, the plaster includes water or an organic liquid ingredient, which is added to the pressure sensitive adhesive layer. Yet more preferably, the organic liquid ingredient is glycol, olive oil, castor oil, squalane, orange oil, mineral oil, $C_{6-20}$ fatty acid, $C_{6-20}$ fatty acid ester or $C_{1-20}$ alcohol. In preferred embodiments, the skin contact base provides sustained release.

In preferred embodiments of the invention, the epithelial tissue is skin tissue.

Preferred embodiments of the invention are directed to a method of treating diabetes in a human subject which includes administration of any of the the topical preparations described above to a human subject.

A preferred embodiment of the invention is directed to a method for treating diabetes in a human subject, including the steps of
  providing a topical preparation which includes a peptide with incretin hormone activity and a transepithelial carrier;
  placing the topical preparation in contact with the skin of a patient such that said active agent is released topically onto the skin of the patient; and
  delivering an effective dose of the peptide with incretin hormone activity to stimulate the secretion of insulin in vivo in the human subject without inducing serious nausea and/or vomiting, wherein the transepithelial carrier includes sufficient amino, guanidine or amidino groups to increase the delivery of the active agent across intact animal skin tissue layers compared to delivery of the peptide in the absence of the transepithelial carrier. In preferred embodiments, the concentration of the peptide with incretin hormone activity is from 0.001% to 70%, and the concentration of the transepithelial carrier is from 0.001% to 70%.

In preferred embodiments, the topical preparation is a conjugate having one of the following structures, V or VI:

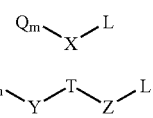

wherein:
Q includes the transepithelial carrier;
L includes the peptide;
X is a linkage formed between a functional group on the peptide and a functional group on the carrier;
Y is a linkage formed between a functional group on the linker and a functional group on the carrier;
Z is a linkage formed between a functional group on the peptide and a functional group on the linker;
T is a small oligopeptide linker; and
m is an integer from 1-5.

In preferred embodiments, structures V and VI are capable of degradation by hydrolysis or glutathione-assisted reduction to release the peptide with incretin hormone activity in its bioactive form. In preferred embodiments, X, Y and Z are independently selected from —S—S—, —C(=O)O—, —C(=O)S—, —C(=O)NH—, —C(=S)NH—, —OC(=O)NH—, —NHC(=O)NH—, —CA=N—, an acetal linkage, a semi-acetal linkage, —SONH—, and —SO$_2$NH—, wherein A is H, alkyl or aryl.

In some preferred embodiments, the peptide and the transepithelial carrier are associated through noncovalent interactions such as electrostatic interaction, hydrogen bonding, π-stacking interaction and van der Waal interaction.

In preferred embodiments, the transepithelial carrier includes a mixture of a monomeric peptide and dimeric forms thereof. Preferably, the transepithelial carrier includes 5 to 50 amino acids, wherein at least 3 amino acids are arginines or lysines or analogs thereof. Preferably, at least one amino acid in the transepithelial carrier is a D-amino acid. In some preferred embodiments, all of the amino acids in the transepithelial carrier are D-amino acids.

In preferred embodiments, the transepithelial carrier includes at least one cysteine amino acid residue. More preferably, the transepithelial carrier includes a peptide monomer, a homodimer thereof, or a mixture of the monomers and the homodimers bound to the peptide with incretin activity though a disulfide bond. In preferred embodiments, at least one amino acid in the transepithelial carrier is a D-amino acid. In some preferred embodiments, all of the amino acids in the transepithelial carrier are D-amino acids.

In preferred embodiments, the peptide with incretin activity includes at least one cysteine amino acid residue, wherein the at least one cysteine is introduced by addition or replacement, or is innately present in the peptide with incretin activity. Preferably, the cysteine amino acid residue is attached to the N-terminus or the C-terminus of the peptide with incretin activity, or the cysteine amino acid residue replaces one of the serine amino acid residues in the peptide with incretin activity.

In a preferred embodiment, the peptide with incretin activity includes the amino acid sequence:

```
                                          (SEQ ID NO: 6)
HGEGTFTSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a preferred embodiment, the peptide with incretin activity includes the amino acid sequence:

```
                                          (SEQ ID NO: 33)
HSDGTFITSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a preferred embodiment, the peptide with incretin activity includes the amino acid sequence:

```
HAEGTFTSDV SSYLEGOAAK EFIAWLVKGR    (SEQ ID NO: 7)
``` wherein the cysteine amino acid residue is attached to the N-terminus or the C-terminus of the amino acid sequence, or the cysteine amino acid residue replaces one of the serine amino acid residues in the amino acid sequence.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. In yet more preferred embodiments, the transepithelial carrier is a peptide monomer, a homo-dimer thereof, or a mixture of the monomers and the homodimers bound to the peptide with incretin activity through a disulfide bond. In yet more preferred embodiments, at least one amino acid in the transepithelial carrier is a D-amino acid. In a highly preferred embodiment, all of the amino acids in the transepithelial carrier are D-amino acids. Preferably, the cysteine amino acid residue is attached to the N-terminus or the C-terminus of the peptide with incretin activity, or the cysteine amino acid residue replaces one of the serine amino acid residues in the peptide with incretin activity.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. More preferably, the peptide with incretin activity includes the amino acid sequence:

```
                                          (SEQ ID NO: 6)
HGEGTFTSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. Preferably, the peptide with incretin activity includes the amino acid sequence:

```
                                          (SEQ ID NO: 33)
HSDGTFITSDL SKQMEEEAVR LFIEWLKNGG PSSGAPPPS
``` and the cysteine amino acid residue is attached to the N-terminus or the C-terminus of the amino acid sequence, or the cysteine amino acid residue replaces one of the serine amino acid residues in the amino acid sequence.

In a more preferred embodiment, the transepithelial carrier includes 5-50 amino acids. At least 3 amino acids of the transepithelial carrier are arginines or lysines or analogs thereof, and the transepithelial carrier includes at least one cysteine amino acid residue. The peptide with incretin activity includes at least one cysteine amino acid residue, which is introduced by addition or replacement, or is innately present in the peptide with incretin activity. Preferably, the peptide with incretin activity includes the amino acid sequence:

HAEGTFTSDV SSYLEGOAAK EFIAWLVKGR    (SEQ ID NO: 7)

and the cysteine amino acid residue is attached to the N-terminus or the C-terminus of the amino acid sequence, or the cysteine amino acid residue replaces one of the serine amino acid residues in the amino acid sequence.

In some preferred embodiments, the transepithelial carrier includes at least one peptide which includes a guanidinium group having the following structure (I):

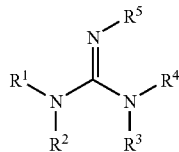

wherein R1, R2, R3, R4 and R5 are each individually selected from hydrogen, optionally substituted C1-C12 alkyl, optionally substituted C2-C12 alkenyl or optionally substituted C2-C12 alkynyl groups with the proviso that R1, R2, R3, R4 and R5 are not all hydrogen. More preferably, the alkyl, alkenyl or alkynyl groups are further substituted with other alkyl, alkenyl, alkynyl or aromatic groups, O, N, S, F, Cl, Br, P, and/or Si.

In some preferred embodiments, any one of the three nitrogen atoms in the guanidinium group participate in zero or one ring system with the proviso that no two nitrogen atoms in the guanidinium group participate in the same ring system.

In alternate preferred embodiments, any two of the three nitrogen atoms in the guanidinium group participate in the same ring system, and the remaining nitrogen atom in the guanidinium group participates in zero or one ring system, with the proviso that if the remaining nitrogen atom in the guanidinium group participates in the one ring system, the one-ring system is not fused to the ring system containing the two nitrogen atoms in the guanidinium group.

In alternate preferred embodiments, any two of the three nitrogen atoms in the guanidinium group participate in the same ring system, and the remaining nitrogen atom in the guanidinium group participates in a one ring system that is fused to the ring system containing the two nitrogen atoms in the guanidinium group.

In some preferred embodiments, the transepithelial carrier includes a peptide which contains a structure of the formula (II):

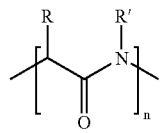

wherein R includes a guanidinium headgroup, R' is H, and n is an integer from 6 to 40. In preferred embodiments, one or more of the peptide bonds is replaced with at least one selected from —C(=O)NHO—, —C(=O)NHNH—, —S(=O)(=O)NR—, —P(=O)(—OR)NR'—, —CH2NR—, —CH2CH2C(=O)NR—, —C(=O)O—, —C(=S)NR—, —S(=O)(=O)CH2—, —SOCH2— and —CH2OC(=O)NR—.

In preferred embodiments, the transepithelial carrier includes a structure of formula (III):

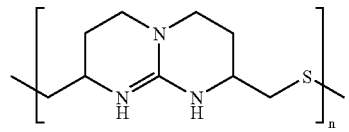

wherein n is an integer from 6 to 40.

In preferred embodments, the transepithelial carrier includes a peptoid of formula (IV):

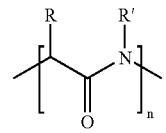

wherein either R or R' includes a guanidinium headgroup and n is the number of monomeric units in the peptoid. Preferably, the guanidinium headgroup is linked to the α carbon atom or α nitrogen atom through a linkage. More preferably, the linkage includes C, O, N, S, F, Cl, Br, P and/or Si atoms. More preferably, the linkage is 1-30 atoms in length.

In preferred embodiments, the peptide with incretin hormone activity is a therapeutic for a disease which is type 2 diabetes, obesity, cardiovascular disease and/or Alzheimer's disease. In preferred embodiments, the peptide with incretin hormone activity is glucagon-like peptide-1 (GLP-1), glucose-dependent insulinotropic polypeptide (GIP), exendin-4 or analogs thereof. In preferred embodiments, the peptide with incretin hormone activity is targeting glucagon-like peptide-1 receptors and glucose-dependent insulinotropic polypeptide receptors.

In preferred embodiments of the invention, the epithelial tissue is skin tissue.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

R7 transdermal delivery; and Panel C shows the evidence of Ex-4-L-R7 on transdermal delivery.

Figure 3:
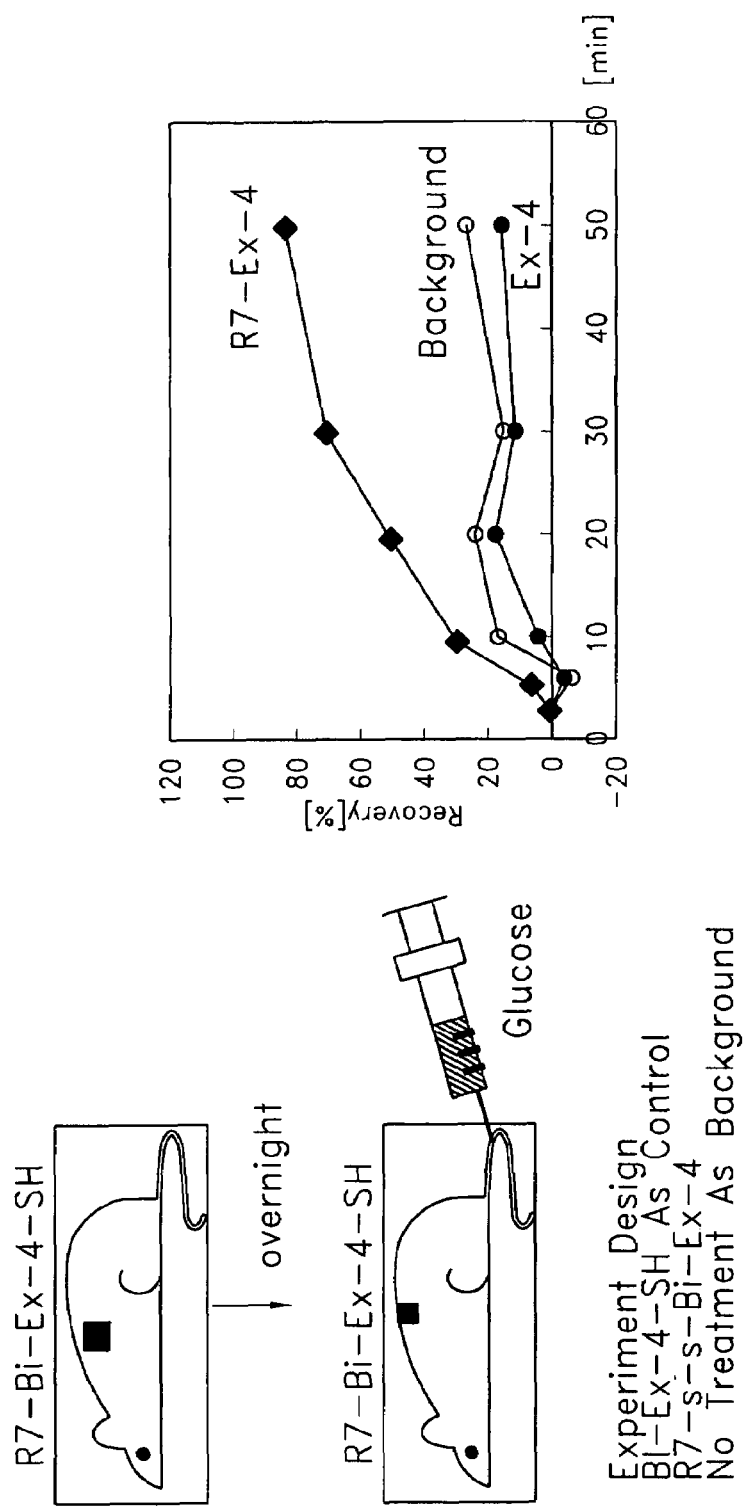

FIG. 3 shows R7 mediated transdermal Ex4 therapeutical studies on blood glucose recovery in nude mouse after intravenous glucose challenge. Panel A shows the schematic of the experiment and Panel B shows the effect of R7-Ex4 on glucose recovery.

Figure 4:
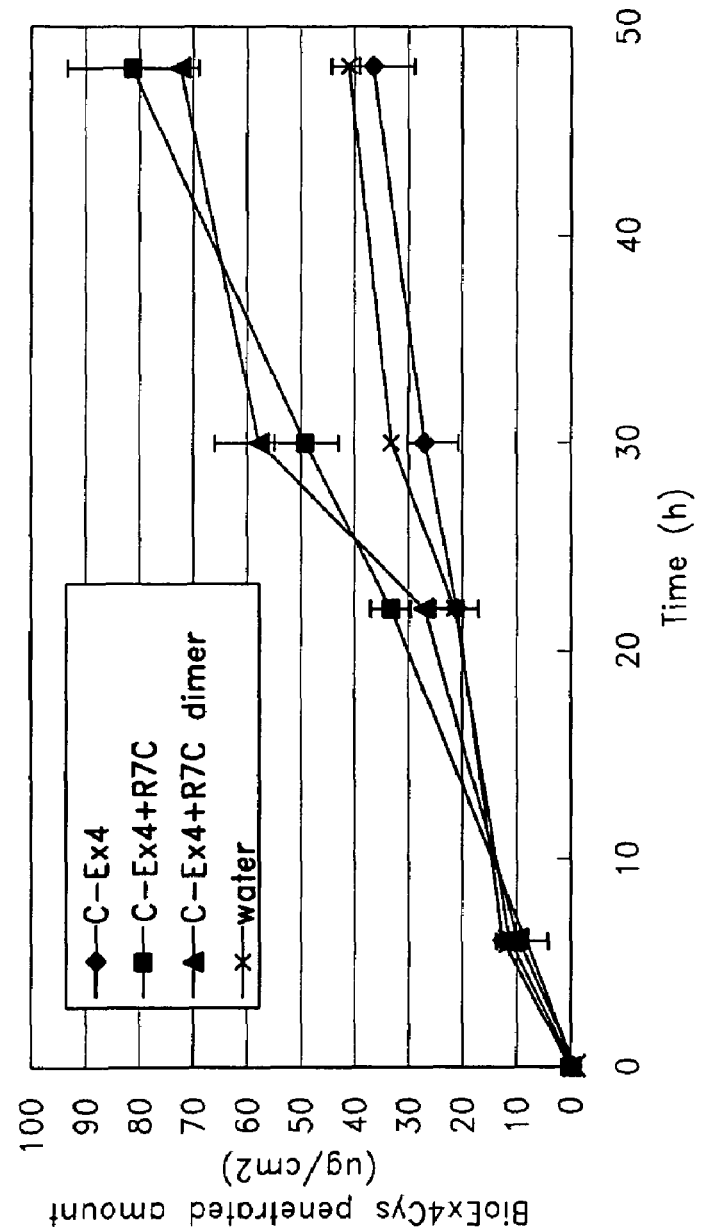

FIG. 4 shows the effect of R7 mediated Ex4 on penetration of human skin.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Definitions

The term "epithelial" is used in its usual sense and relates to the epithelium, the outside layer of cells that covers all the free, open surfaces of the body including the skin, and mucous membranes that communicate with the outside of the body.

The term "transepithelial" refers to entry of a substance such as a drug through the epithelium, including direct topical application as well as application using a support material such as a patch.

The term "transdermal" or "transcutaneous" refers to entry of a substance such as a drug through the dermis or skin and includes direct topical application as well as application using a support material such as a patch.

"Transdermal carrier" or "transdermal transporter" refers to any compound which facilitates movement of a compound such as a drug across the dermis.

"Protein transduction domain (PTD)" or "cell penetrating peptide (CPP)" refers to a class of transdermal carriers that includes any peptide capable of mediating membrane translocation of a cargo when the peptide is covalently or noncovalently attached to the cargo.

"Transdermal preparation" refers to a composition which includes at least one compound to be transported across at least one skin layer and additional components to facilitate the transport. The additional materials may include one or more transepithelial carriers as well as a solid support such as a patch material. The patch material may include one or more adhesives to attach to the skin. In preferred embodiments, the compound to be transported is a peptide with incretin hormone activity. In preferred embodiments, the transepithelial preparation includes at least one PTD. Optionally, other components may be included to enhance transepithelial transport as discussed below.

"Peptide" refers to a compound made up of amino acids joined by peptide bonds. The amino acids may be D- or L-amino acids or a mixture thereof. The peptide chain may be linear or branched. Generally, peptides contain at least two amino acid residues and are generally less than 50 amino acids in length.

"Cargo" refers to the one or more compounds that are transported across at least one skin layer. In preferred embodiments, the cargo is a peptide with incretin hormone activity.

"Carrier-cargo complex" refers to a complex or conjugate of the compound to be transported and the transporter. In preferred embodiments, both the carrier and the cargo are peptides. The cargo is a peptide with incretin hormone activity and the carrier is preferably a PTD, more preferably, a peptide which is rich in amino, guanidine and/or amidino groups. The carrier may be complexed to the cargo by either covalent or non-covalent interactions as discussed below.

"Analog" refers to a functional variant having a similar amino acid sequence and retaining at least some functional properties. In the context of the present invention, an analog of GLP-1 or exendin refers to a functional variant having a similar amino acid sequence to GLP-1 and retaining the insulinotropic properties, at least to some extent of the related GLP-1, exendin or agonist thereof. Similar amino acid sequence refers to the amount of sequence identity between the analog and the related GLP-1, exendin or agonist thereof. Preferably, the sequence identity is at least 50%, more preferably, at least 60%, more preferably, at least 70%, more preferably, at least 80%, more preferably, at least 90%, and yet more preferably, at least 95%.

A "functional variant" refers to a derivative that has an activity that can be substituted for one or more activities of a particular exendin or GLP-1 or an agonist thereto.

The term "innate" is taken to have its usual meaning and, in particular, is used in the context of a peptide that innately contains a particular amino acid. A peptide innately contains a particular amino acid if the particular amino acid is present in the native peptide, without need for modification such as by chemical or recombinant means.

Peptides with Incretin Hormone Activities

By definition, incretin hormones are hormones that cause an increase in the amount of insulin released when glucose levels are normal or particularly when they are elevated. There are two known incretin hormones in humans: glucose-dependent insulinotropic polypeptide (GIP) and glucagon-like peptide-1 (GLP-1). Currently, there is much focus on GLP-1 as the basis for a potential new treatment paradigm for diabetes, obesity, cardiovascular diseases and Alzheimer's disease.

GLP-1 is a product of the preproglucagon gene. It is synthesized in the L-cells of the lower intestinal tract in response to food intake. In the pancreas, GLP-1 potentiates glucose-induced insulin secretion from the β-cells in a strictly glucose dependent manner. GLP-1 has a number of other functionally important effects that are relevant for treating type 2 diabetes: stimulation of all steps of insulin biosynthesis, restoration of glucose sensitivity to the islets, and stimulation of increased expression of the glucose transporter GLUT-2 and glucokinase. GLP-1 also has trophic effects on β-cells: stimulation of β-cell proliferation, enhancement of the differentiation of new β-cells from progenitor cells in the pancreatic duct epithelium, and inhibition of both cytokine and fatty acid-induced apoptosis in β-cells. GLP-1 inhibits glucagon secretion, which then leads to reduced hepatic glucose output. In the gut, GLP-1 is a potent inhibitor of motility and gastric emptying and has also been shown to inhibit gastric acid secretion. The inhibition of gastric emptying leads to decreased food intake and reduced body weight. Thus the current belief is that the GLP-1 compound class may be able to control the progression of the type 2 diabetes disease not only by controlling blood glucose but also via several other effects.

The clinical potential of the GLP-1 compound class in diabetes treatment has been demonstrated by their glucose lowering effects. In one published study, natural GLP-1 was administered to diabetes patients through subcutaneous pump infusion for up to 6 weeks. This study demonstrated a potential for GLP-1 to rapidly lower fasting blood glucose by 4-5 mM, mainly with the first week of treatment. No other currently available diabetes drugs, including sulfonylureas, metformin or insulin sensitizers have this effect. In addition, unlike all the other currently available diabetes drugs, GLP-1 can uniquely achieve efficient glucose control without inducing serious side effects such as hypoglycemia and weight gain.

The biological function of GLP-1 is through interaction with the GLP-1 receptor, a G-protein-coupled receptor. Although predominantly located in pancreatic islets, GLP-1 receptors are also expressed in the heart and the brain. The existence of GLP-1 receptors in the heart, along with the benefits of GLP-1 in reducing blood glucose, may provide the basis for the use of GLP-1 to treat cardiovascular complications. Emerging evidence also suggests GLP-1 compound class has the potential to treat Alzheimer's disease. GLP-1 has been demonstrated to induce neurite outgrowth and to protect against excitotoxic cell death and oxidative injury in cultured neuronal cells. Moreover, GLP-1 and exendin-4 were shown to reduce endogenous levels of β-amyloid peptide (Aβ) in mouse brain and to reduce levels of β-amyloid precursor protein in neurons.

There are two subclasses of GLP-1 in clinical development. One is natural GLP-1. The other is exendin-4 from Lilly and Amylin. Exendin-4 is currently in phase 3 clinical development and showed effects to stimulate β-cell growth, replication and neogenesis. There are a number of other GLP-1 analogs that are currently under development from a number of companies. Novo Nordisk has completed phase 2 clinical trials with liraglutide as a once daily injection therapy. Liraglutide is equipotent to GLP-1 and has a half-life that is more than 10-fold longer than exendin-4. Conjuchem is developing a reactive GLP-1 analog CJC-1131. CJC-1131 was modified to protect against DPP-IV degradation. CJC-1131 was also designed to covalently bond to albumin after sc injection so that the conjugate will have the half-life of albumin. Human Genome Sciences is in the discovery phase with Albugon, a fusion protein between a GLP-1 analog and albumin. Zealand Pharma has announced GLP-1 analog ZP10A and exendin-4 analog ZP10A. Ipsen has announced the protease stabilized GLP-1 analog BIM-51077.

The peptide with incretin hormone activity may also be any peptide capable of binding to either a glucagon-like peptide 1 receptor or a glucose-dependent insulinotropic polypeptide receptor. The peptides with incretin hormone activity include glucagon-like peptide (GLP-1), glucose-dependent insulinotropic peptide (GIP) and GLP-1 agonists such as exendin 4. Optionally, the peptide with incretin hormone activity may be modified with a cysteine residue at the N or C terminal or replacing one of the serine residues. Peptides with incretin hormone activities include the following which are also listed in Tables 1 and/or 2: GLP-1, GIP, Exendin-3, Exendin-4, Liraglutide, CJC-1131 and ZP10A.

The clinical potential of the peptides with incretin hormone activities lies in the treatment of chronic disorders including diabetes, obesity, cardiovascular diseases and Alzheimer's disease. Efficiently administering these peptides is the major challenge for development into useful therapeutic agents for the treatment of chronic disorders. In practice, there is an urgent need for safe, convenient and cost-effective alternatives to injection, the only feasible delivery route currently available for peptide drugs. Not only does injection increase the burden of patients and their health care providers, the peak concentrations of GLP-1 compound class induced by injection also caused nausea and vomiting in the patients. Transepithelial delivery route is extremely attractive for the GLP-1 compound class. Efficient transepithelial delivery depends on the creation of a transepithelial path as well as improving the properties of the drugs. For compounds with the size of GLP-1 and exendin-4, these properties consist of:

(1) Desirable physical property (water solubility, logP, etc.)
(2) Stability to protease (DPP-IV, etc.) action Improvement of these properties is achievable through chemical modification of the peptides. These modifications include phosphorylation, glycosylation, crosslinking, acylation, proteolytic cleavage, linkage to an antibody molecule, membrane molecule or other ligand.

Embodiments of the invention are directed to delivery of one or more peptides with incretin hormone activity through the skin of a patient using a transepithelial carrier. Peptides with incretin hormone activity include GLP-1, exendins and analogs thereof. Non-limiting examples of peptides with incretin hormone activity are provided in Table 2.

TABLE 2

Table of Sequences with incretin hormone activity
Table of Sequences

| SEQ ID NO | Clone Name | Length | Type |
|---|---|---|---|
| 1 | GLP-1 | 204 | Protein |
| 2 | exendin-4 | 87 | Protein |
| 3 | exendin 3 | 39 | Protein |
| 4 | exendin 2 | 35 | Protein |
| 5 | exendin 1 | 38 | Protein |
| 6 | exendin-4 | 39 | Protein |
| 7 | GLP-1 | 30 | Protein |
| 8 | GLP-1 agonist | 30 | Protein |
| 9 | GLP-1 agonist | 28 | Protein |
| 10 | GLP-1 agonist | 28 | Protein |
| 11 | GLP-1 agonist | 28 | Protein |
| 12 | GLP-1 agonist | 28 | Protein |
| 13 | GLP-1 agonist | 28 | Protein |
| 14 | GLP-1 agonist | 28 | Protein |
| 15 | GLP-1 agonist | 28 | Protein |
| 16 | GLP-1 agonist | 28 | Protein |
| 17 | GLP-1 agonist | 28 | Protein |
| 18 | GLP-1 agonist | 28 | Protein |
| 19 | GLP-1 agonist | 28 | Protein |
| 20 | GLP-1 agonist | 28 | Protein |
| 21 | GLP-1 agonist | 28 | Protein |
| 22 | GLP-1 agonist | 28 | Protein |
| 23 | GLP-1 agonist | 28 | Protein |
| 24 | GLP-1 agonist | 28 | Protein |
| 25 | GLP-1 agonist | 28 | Protein |
| 26 | GLP-1 agonist | 28 | Protein |
| 27 | GLP-1 agonist | 28 | Protein |
| 28 | GLP-1 agonist | 28 | Protein |
| 29 | GLP-1 agonist | 28 | Protein |
| 30 | GLP-1 agonist | 28 | Protein |
| 31 | exend-4 (mod) | 40 | Protein |
| 33 | exendin | 40 | Protein |
| 34 | GIP | 153 | Protein |
| 35 | ZP10A | 45 | Protein |

Peptide compounds with incertin hormone activity useful in the invention may be prepared by chemical synthesis or by using recombinant DNA techniques. Exendin or GLP-1 agonist analogs or derivatives are included within the methods of the present invention. Analogs or derivatives are functional variants of an exendin or GLP-1 having similar amino acid sequence and retaining, to some extent, the insulinotropic properties of the related exendin or GLP-1 or agonists thereto. By a functional variant is meant the derivative has an activity that can be substituted for one or more activities of a particular exendin or GLP-1 or an agonist thereto. Preferred functional variants retain all of the activities of a particular exendin or GLP-1 or an agonist thereto, however, the functional variant may have an activity that, when measured quantitatively, is stronger or weaker, as measured in functional assays, for example, such as those disclosed herein. Derivatives have at least about 50% sequence similarity, preferably about 70%, more preferably about 90%, and even more preferably about 95% sequence similarity to the related exendin or GLP-1, or agonist thereto. "Sequence similarity" refers to "homology" observed between amino acid sequences in two different polypeptides, irrespective of polypeptide origin.

Derivatives include modification occurring during or after translation, for example, by phosphorylation, glycosylation, crosslinking, acylation, proteolytic cleavage, linkage to an antibody molecule, membrane molecule or other ligand.

Derivatives can be produced using standard chemical techniques and recombinant nucleic acid molecule techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Sambrook, et al., Molecular Cloning, Cold Spring Harbor Laboratory Press (1989).

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, flumaric acid and camphorsulfonic acid. Salts prepared with bases include ammonium salts, alkali metal salts, e.g. sodium and potassium salts, and alkali earth salts, e.g. calcium and magnesium salts. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compositions including the peptides with incretin hormone activity described above can also be formulated as pharmaceutically acceptable salts (e.g., acid addition salts) and/or complexes thereof. Pharmaceutically acceptable salts are non-toxic salts at the concentration at which they are administered.

Pharmaceutically acceptable salts include acid addition salts such as those containing sulfate, hydrochloride, phosphate; sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Transepithelial Carriers for the Delivery of Peptides with Incretin Hormone Activities Creation of a transepithelial path is critical for transepithelial delivery. There are various ways available for creating the transepithelial path, including microneedle and the use of chemical enhancers, etc. Covalently or noncovalently conjugating drugs with a transepithelial carrier has the potential advantage of not causing skin inflammation, a side effect associated with other transepithelial delivery methods. In a recent paper, Rothbard et al. (Rothbard, J. B.; Garlington, S.; Lin, Q.; Kirschberg, T.; Kreider, E.; McGrane, P. L.; Wender, P. A.; Khavari, P. A. "Conjugation of arginine oligomers to cyclosporine A facilitates topical delivery and inhibition of inflammation", Nature Medicine, 2000, 6, 1253-1257.) conjugated a heptamer of arginine to cyclosporine A through a pH-sensitive linker to produce R7-CsA. In contrast to unmodified cyclosporine A, which failed to penetrate skin, topically applied R7-CsA was efficiently transported into cells of mouse and human skin. R7-CsA reached dermal T lymphocytes and inhibited cutaneous inflammation.

The arginine heptamer belongs to a compound class generally known as protein transduction domain (PTD) or cell penetrating peptide (CPP). This compound class includes any peptide capable of mediating membrane translocation of a cargo when the said peptide is covalently or noncovalently attached to the said cargo. There are a vast number of peptide sequences in the published scientific literature that can mediate the translocation of a cargo across a cell membrane. Arginine oligomer is the first PTD investigated which showed efficiency in translocating a cargo across skin tissues.

Human skin is made of three layers. Stratum corneum, located on the outer surface of the skin, is a non-living layer of keratin-filled cells surrounded by a lipid-rich extracellular matrix that provides the primary barrier to drug delivery into skin. The epidermis below is a viable tissue devoid of blood vessels. Just below the dermal-epidermal junction, the dermis contains capillary loops that can take up transepithelially administered drugs for systemic distribution. For most molecules the stratum corneum is the rate-limiting barrier to drug delivery. Stratum corneum also bears some similarity to the cell membrane in that both tissues are lipid-rich.

The arginine heptamer was derived from modification of the human immunodeficiency virus (HIV) tat protein, an 86-residue protein that can enter cells when added to the medium of cells in culture. Many peptides derived from HIV tat protein have been shown to have cell penetrating effects. The minimum domain responsible for the translocation effects consists of residues 49-57. HIV tat (49-57) is rich in arginine and highly basic. It was further demonstrated that the guanidinium headgroups in HIV tat (49-57) are principally responsible for its uptake into cells. Replacing all nonarginine residues in HIV tat (49-57) with arginines provided transporters that exhibit superior rates of uptake. Recently, it was proposed that the water-soluble, positively charged guanidinium headgroups of the transporter form bidentate hydrogen bonds with the H-bond acceptor functionality on the cell surface, and the resultant ion pair complexes partition into the lipid bilayer and migrate across the membrane (J. B. Rothbard et al. "Role of Membrane Potential and Hydrogen Bonding in the Mechanism of Translocation of Guanidinium-Rich Peptides into Cells", J. Am. Chem. Soc. (2004), 126, 9506-9507). This mechanism at least partly explains why arginine rich oligo peptides can efficiently create a transdermal path for drug delivery, since two of the three known transdermal route involve partition of drugs between aqueous and lipid phases: In the transcellular route, a drug molecule penetrates across the stratum corneum through a series of events that include partition between bilayer lipid and keratin-filled cells followed by diffusion through the hydrated keratin. The intercellular lipid route provides the principal pathway by which most small, uncharged molecules traverse stratum corneum by moving through the continuous lipid domains between the keratinocytes.

Some of the best characterized arginine rich PTD include peptides derived from the homeodomain of the Drosophila homeoprotein antennapedia (pAntp), penetratin and peptides derived from HIV tat. Representative sequences are:

```
pAntp(43-58); penetratin
RQIKIWFQNRRMKWKK                    (SEQ ID NO: 36)

retro-inverso pAntp(43-58)
kkwkmrrnqfwvkvqr                    (SEQ ID NO: 37)
(all D-amino acids)

W/R penetratin
RRWRRWWRRWWRRWRR                    (SEQ ID NO: 38)

pAntp(52-58)
RRMKWKK                             (SEQ ID NO: 39)

HIV tat(49-57)
RKKRRQRRR                           (SEQ ID NO: 40)

HIV tat(48-60)
GRKKRRQRRRPPQ                       (SEQ ID NO: 41)

HIV tat(47-57)
YGRKKRRQRRR                         (SEQ ID NO: 42)

r7
rrrrrrr                             (SEQ ID NO: 43)
(all D-amino acids)

r9
rrrrrrrrr                           (SEQ ID NO: 44)
(all D-amino acids)
```

The present invention provides compositions and methods that provide for transport of peptides with incretin hormone activity, into and across one or more epithelial layers, preferably one or more layers of an animal skin tissue. The methods involve contacting the skin or other epithelial tissue with a conjugate that includes the peptide with incretin hormone activity either covalently linked to or non-covalently associated with a transepithelial transporter. The transepithelial transporters of the invention are molecules that include sufficient guanidino or amidino moieties to increase delivery of the conjugate into and across one or more intact skin or other epithelial tissue layers. The methods and compositions are useful for treatment of diabetes mellitus and related diseases including obesity and Alzheimer's Disease.

The transepithelial carrier may be any composition which facilitates transfer of the peptide with incretin hormone activity through epithelial tissue such as skin. Preferably, the transepithelial carrier is a peptide which contains one or more amino, guanidine and/or amidino groups. The term "guanidinium group" refers to a moiety with the following structure (I):

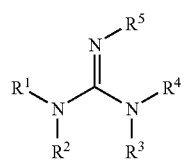

In formula (I), $R^1$, $R^2$, $R^3$, $R^4$ and $R^5$ can be hydrogen atoms, alkyl, alkenyl or alkynyl groups. In certain embodiments, $R^1$, $R^2$, $R^3$, $R^4$ and $R^5$ cannot all simultaneously be hydrogen atoms. The alkyl, alkenyl and alkynyl groups can be further substituted with other alkyl, alkenyl, alkynyl or aromatic groups as well as functional groups with heteroatoms such as O, N, S, F, Cl, Br, P, and/or Si.

Any one of the three nitrogen atoms in the guanidinium group may independently participate in zero or one ring system. In certain embodiment, no two nitrogen atoms in the guanidinium group participate in the same ring system.

In other embodiments, any two of the three nitrogen atoms in the guanidinium group may participate in the same ring system, and the remaining nitrogen atom in the guanidinium group participates in zero or one ring system, and if the remaining nitrogen atom in the guanidinium group participates one ring system, this ring system is not fused to the ring system containing the two nitrogen atoms in the guanidinium group.

In some embodiments, any two of the three nitrogen atoms in the guanidinium group participate in the same ring system, and the remaining nitrogen atom in the guanidinium group participates in one ring system that is fused to the ring system containing the two nitrogen atoms in the guanidinium group.

The aforementioned ring systems may be 4-, 5-, 6- or 7-membered. Each ring system can contain zero, one, or more multiple bonds, or can be aromatic. Each of the ring systems can be fused to zero or one ring system. Each of the ring systems can be substituted with alkyl, alkenyl, alkynyl or aromatic groups as well as functional groups with heteroatoms such as O, N, S, F, Cl, Br, P, and/or Si. Two ring systems are fused if they share one common bond.

The term "amidino group" refers to a moiety with the formula: —C(=NH)(NH₂). The amino, guanidine, and/or amido groups may be found on the amino acids that constitute the transport peptide. Lysine and Arginine are particularly preferred amino acid residues for transport peptides.

In certain embodiments, the peptide is a structure of the general formula (II):

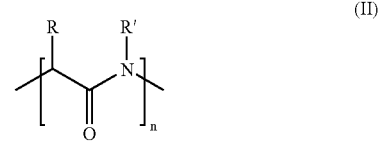

where the guanidinium headgroup is part of R, R' is H, and n is the number of monomeric amino acid units in this peptide. In the peptide structure II), the structural fragment —C(=O)NR'— is called the peptide bond. The exact nature of this structural fragment has minimal impact on the translocation efficiency of the transepithelial carrier. Therefore, any one of the peptide bonds can be replaced with one of the following alternatives: —C(=O)NHO—, —C(=O)NHNH—, —S(=O)(=O)NR—, —P(=O)(—OR)NR'—, —CH₂NR—, —CH₂CH₂C(=O)NR—, —C(=O)O—, —C(=S)NR—, —S(=O)(=O)CH₂—, —SOCH₂— and —CH₂OC(=O)NR—.

Other transepithelial carriers may also be used, for example those including the a structure of the formula (III):

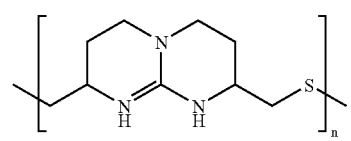

The transepithelial carrier can also be a peptoid. In a peptoid, e.g., of the formula (IV),

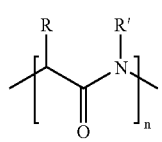

the guanidinium headgroup is part of R', and the R group can be hydrogen or one of the 20 naturally occurring amino acid side chains. The guanidinium headgroup may be a part of R or R', and may be linked to the α carbon atom or α nitrogen atom through a linkage. The length of the linkage may be from 1-30 atoms and may contain heteroatoms such as O, N, S, F, Cl, Br, P and/or Si in addition to carbon. Any atom in the linkage may be substituted with alkyl, alkenyl, alkynyl and/or aromatic groups as well as functional groups with heteroatoms such as O, N, S, F, Cl, Br, P, or Si. Any two or more atoms in the linkage may participate in a ring structure.

In preferred embodiments, the transepithelial carrier is a transport peptide. Preferably, the length of the transport peptide is 3-60 amino acids, more preferably 5-50 amino acids. Preferably, at least 20% of the amino acids are arginine or lysine. More preferably, at least 35% of the amino acids are arginine or lysine. More preferably, at least 50% of the amino acids are arginine or lysine. More preferably, at least 60% of the amino acids are arginine or lysine. More preferably, at least 80% of the amino acids are arginine or lysine. A highly preferred transepithelial peptide carrier is R7C which is 7 arginines and one cysteine. The amino acids may be natural or non-natural amino acids. For example, the transepithelial carrier may contain one or more D-amino acids. The transport peptides are prepared by any means known in the art including chemical synthesis and recombinant methods.

The transepithelial transporters of the invention are molecules that have sufficient guanidino and/or amidino moieties to increase delivery of a compound with incretin hormone activity into and across one or more skin layers. The transepithelial transporters generally include a backbone structure to which is attached the guanidino and/or amidino sidechain moieties. In some embodiments, the backbone is a polymer that consists of subunits (e.g., repeating monomer units), at least some of which subunits contain a guanidino or amidino moiety. In some preferred embodiments, the monomer units are joined by disulfide bonds. Preferably, the disulfide bonds are provided by cysteine residues on the terminal ends of the transepithelial transporter. In some embodiments, a heterogenous transepithelial transporter is employed. For example, the transepithelial transporter may include both monomer and dimer units.

The transepithelial transporter typically displays at least 5 guanidino and/or amidino moieties, and more preferably 7 or more such moieties. Preferably, the transepithelial transporter has 25 or fewer guanidino and/or amidino moieties, and often has 15 or fewer of such moieties. In some embodiments, the transepithelial transporter consists essentially of 50 or fewer subunits, and can consist essentially of 25 or fewer, 20 or fewer, or 15 or fewer subunits. The transepithelial transporter can be as short as 5 subunits, in which case all subunits include a guanidino or amidino sidechain moiety. The transepithelial transporter can have, for example, at least 6 subunits, and in some embodiments have at least 7 to 10 subunits. Generally, at least 50% of the subunits contain a guanidino or amidino sidechain moiety. More preferably, at least 70% of the subunits, and sometimes at least 90% of the subunits in the transepithelial transporter contain a guanidino or amidino sidechain moiety.

Some or all of the guanidino and/or amidino moieties in the transepithelial transporters can be contiguous. For example, the transepithelial transporters can include from 6 to 25 contiguous guanidino and/or amidino-containing subunits. Seven or more contiguous guanidino and/or amidino-containing subunits are present in some embodiments. In some embodiments, each subunit that contains a guanidino moiety is contiguous, as exemplified by a polymer containing at least six contiguous arginine residues.

The transepithelial transporters are generally peptides. Arginine residues or analogs of arginine can constitute the subunits that have a guanidino moiety. Such an arginine-containing peptide can be composed of either all D-, all L- or mixed D- and L-amino acids, and can include additional amino acids, amino acid analogs, or other molecules between the arginine residues. Optionally, the transepithelial transporter can also include a non-arginine residue to which a compound to be delivered is attached, either directly or through a linker. In some embodiments, the use of at least one D-arginine in the transepithelial transporter is preferred. In some cases, the transepithelial transporters are at least about 50% D-arginine residues. In some embodiments, transporters in which all of the subunits are D-arginine residues are used. Compositions containing exclusively D-amino acids have the advantage of decreased enzymatic degradation.

Preferably, the transepithelial transporter is linear. In a preferred embodiment, a peptide with incretin hormone activity is attached to a terminal end of the transepithelial transporter. In preferred embodiments, this attachment is through a disulfide linkage. In some preferred embodiments, the disulfide linkage is provided by a terminal cysteine on the peptide with incretin hormone activity linked to a terminal cysteine on the transepithelial transporter. In some embodiments, the peptide with incretin hormone activity is linked to a single transport polymer to form a conjugate. In other embodiments, the conjugate can include more than one transepithelial transporter linked to peptide with incretin hormone activity linked to a single transepithelial transporter.

More generally, it is preferred that each subunit contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character.

The guanidino or amidino moieties extend away from the backbone by virtue of being linked to the backbone by a sidechain linker. The sidechain atoms are preferably provided as methylene carbon atoms, although one or more other atoms such as oxygen, sulfur or nitrogen can also be present.

In some embodiments, the transepithelial transporter is composed of D or L amino acid residues. The amino acids can be naturally occurring or non-naturally occurring amino acids. Arginine (α-amino-δ-guanidinovaleric acid) and α-amino-ε-amidino-hexanoic acid (isosteric amidino analog) are examples of suitable guanidino- and amidino-containing amino acid subunits. The guanidinium group in arginine has a pKa of about 12.5. In some preferred embodiments the transporters are comprised of at least six contiguous arginine residues.

Other amino acids, such as α-amino-β-guanidino-propionic acid, α-amino-γ-guanidino-butyric acid, or α-amino-ε-guanidino-caproic acid (containing 2, 3 or 5 sidechain linker atoms, respectively, between the backbone chain and the central guanidinium carbon) can also be used.

Transepithelial transporters are constructed by any method known in the art. Exemplary peptide polymers can be produced synthetically, preferably using a peptide synthesizer (e.g., an Applied Biosystems Model 433) or can be synthesized recombinantly by methods well known in the art. Recombinant synthesis is generally used when the transepithelial transporter is a peptide which is fused to the peptide with incretin hormone activity.

N-methyl and hydroxy-amino acids can be substituted for conventional amino acids in solid phase peptide synthesis. However, production of transepithelial transporters with reduced peptide bonds requires synthesis of the dimer of amino acids containing the reduced peptide bond. Such dimers are incorporated into polymers using standard solid phase synthesis procedures.

The transepithelial transporters of the invention can be flanked by one or more non-guanidino/non-amidino subunits (such as glycine, alanine, and cysteine, for example), or a linker (such as an aminocaproic acid group), that do not significantly affect the rate of transport through the skin of the conjugates. Also, any free amino terminal group can be capped with a blocking group, such as an acetyl or benzyl group, to prevent ubiquitination in vivo.

Where the transepithelial transporter is a peptoid polymer, one synthetic method involves the following steps: 1) a peptoid polyamine is treated with a base and pyrazole-1-carboxamidine to provide a mixture; 2) the mixture is heated and then allowed to cool; 3) the cooled mixture is acidified; and 4) the acidified mixture is purified. Preferably the base used in step 1 is a carbonate, such as sodium carbonate, and heating step 2 involves heating the mixture to approximately 50° C. for between about 24 hours and about 48 hours. The purification step preferably involves chromatography (e.g., reverse-phase HPLC).

The peptide with incretin hormone activity can be linked to the transepithelial transporter according to a number of embodiments. In one embodiment, the peptide with incretin hormone activity is linked to a single transepithelial transporter, either via linkage to a terminal end of the transepithelial transporter or to an internal subunit within the reagent via a suitable linking group. In a second embodiment, the peptide with incretin hormone activity is attached to more than one transepithelial transporter, in the same manner as above. In a third embodiment, the conjugate contains two peptides with incretin hormone activity attached to each terminal end of the transepithelial transporter. With regard to the first and third embodiments just mentioned, the peptides with incretin hormone activity are generally not attached to any of the guanidino or amidino sidechains so that they are free to interact with the target membrane.

The conjugates of the invention can be prepared by straightforward synthetic schemes. Furthermore, the conjugate products are usually substantially homogeneous in length and composition, so that they provide greater consistency and reproducibility in their effects than heterogeneous mixtures.

The peptides with incretin hormone activity of the invention can be attached covalently to the transepithelial transporter by chemical or recombinant methods.

One or more peptides with incretin hormone activity can be linked to a transepithelial transporter according to the invention via a number of methods known in the art (see, for example, Wong, S. S., Ed., Chemistry of Protein Conjugation and Cross-Linking, CRC Press, Inc., Boca Raton, Fla. (1991), either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the substance across the cell membrane.

Various functional groups (hydroxyl, amino, halogen, etc.) can be used to attach the biologically active agent to the transport polymer. Groups which are not known to be part of an active site of the peptide with incretin hormone activity are preferred, particularly if the polypeptide or any portion thereof is to remain attached to the substance after delivery.

Polymers are generally produced with an amino terminal protecting group, such as Fmoc. The Fmoc may be cleaved from the N-terminus of the completed resin-bound polypeptide so that the agent can be linked to the free N-terminal amine. In such cases, the agent to be attached is typically activated by methods well known in the art to produce an active ester or active carbonate moiety effective to form an amide or carbamate linkage, respectively, with the polymer amino group. Of course, other linking chemistries can also be used.

To help minimize side-reactions, guanidino and amidino moieties can be blocked using conventional protecting groups, such as carbobenzyloxy groups (CBZ), di-t-BOC, PMC, Pbf, N—$NO_2$, and the like.

Coupling reactions are performed by known coupling methods in any of an array of solvents, such as N,N-dimethyl formamide (DMF), N-methyl pyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

The peptides with incretin hormone activity can be attached to the transepithelial transporter by recombinant means by constructing vectors for fusion proteins comprising the polypeptide of interest and the transepithelial transporter, according to methods well known in the art. Generally, the transepithelial transporter component will be attached at the C-terminus or N-terminus of the polypeptide of interest, optionally via a short peptide linker.

The linkage between the transepithelial carrier peptide and the peptide with incretin hormone activity may be covalent or non-covalent. Non-covalent interactions may include electrostatic interaction, hydrogen bonding, π-stacking interaction, and van der Waal interaction. In preferred embodiments, the peptide with incretin hormone activity is attached to the transepithelial transporter using a linkage that is specifically cleavable or releasable. As used herein, "cleaved" or "cleavage" of a conjugate or linker refers to release of the peptide with incretin hormone activity from the transepithelial transporter molecule, thereby releasing an active peptide with incretin hormone activity. "Specifically cleavable" or "specifically releasable" refers to the linkage between the transporter and the peptide with incretin hormone activity being cleaved, rather than the transporter being degraded (e.g., by proteolytic degradation).

In some embodiments, the linkage is a readily cleavable linkage, meaning that it is susceptible to cleavage under conditions found in vivo. Thus, upon passing into and through one or more skin layers, the peptide with incretin hormone activity is released from the transepithelial transporter. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. The linkage can be selected so it is cleavable by an enzymatic activity that is known to be present in one or more layers of skin tissue. For example, the stratum granulosum of skin has a relatively high concentration of N-peptidase activity.

A specifically cleavable linker can be engineered onto a transepithelial transporter molecule. For example, amino acids that constitute a protease recognition site, or other such specifically recognized enzymatic cleavage site, can be used to link the transepithelial transporter to the peptide with incretin hormone activity. Alternatively, chemical or other types of linkers that are cleavable by, for example, exposure to light or other stimulus can be used to link the peptide with incretin hormone activity to the transepithelial transporter.

A conjugate in which a peptide with incretin hormone activity to be delivered and a transepithelial transporter are linked by a specifically cleavable or specifically releasable linker will have a half-life. The term "half-life" in this context refers to the amount of time required after applying the conjugate to skin for one half of the amount of conjugate to become dissociated to release the free agent. The half-life for some embodiments is typically between 5 minutes and 24 hours, and more preferably is between 30 minutes and 2 hours. The half-life of a conjugate can be modified as described below.

In some embodiments, the cleavage rate of the linkers is pH dependent. For example, a linker can form a stable linkage between the peptide with incretin hormone activity and the transepithelial transporter at an acidic pH (e.g., pH 6.5 or less, more preferably about 6 or less, and still more preferably about 5.5 or less). However, when the conjugate is placed at physiological pH (e.g., pH 7 or greater, preferably about pH 7.4), the linker will undergo cleavage to release the agent. Such pH sensitivity can be obtained by, for example, including a functional group that, when protonated (i.e., at an acidic pH), does not act as a nucleophile. At a higher (e.g., physiological) pH, the functional group is no longer protonated and thus can act as a nucleophile. Examples of suitable functional groups include, for example, N and S. One can use such functional groups to fine-tune the pH at which self-cleavage occurs. In some embodiments, the half like of the carrier-cargo complex is between 5 minutes and 24 hours after contact with skin tissue. More preferably, the half life of the carrier-cargo complex is between 30 minutes and 2 hours after skin contact.

In another embodiment, the linking moiety is cleaved through self-immolation. Such linking moieties contain a nucleophile (e.g., oxygen, nitrogen and sulfur) distal to the peptide with incretin hormone activity and a cleavable group (e.g., ester, carbonate, carbamate and thiocarbamate) proximal to the peptide with incretin hormone activity. Intramolecular attack of the nucleophile on the cleavable group results in the scission of a covalent bond, thereby releasing the linking moiety from the peptide with incretin hormone activity.

Linkers may contain one or more of the following functional groups: —S—S—, —C(=O)O—, —C(=O)—, —(=O)NH—, —C(=S)NH—, —OC(=O)NH—, —NHC(=O)NH—, —CA=N—, —SONH— and —SO$_2$NH—, wherein A is selected from the group consisting of H, alkyl and aryl.

The peptide with incretin hormone activity may be separated from the transepithelial carrier peptide by hydrolysis or by glutathione-assisted reduction. Alternatively the peptide with incretin hormone activity and the transepithelial carrier peptide may be associated by non-covalent interactions such as electrostatic interaction, hydrogen bonding, π-stacking interaction and van der Waal interaction. In some embodiments, more than one transepithelial carrier is used to transport peptides with incretin activity. For example, the transepithelial carrier may include one or more of monomers, dimers, trimers, etc. Alternatively, the transepithelial carrier may contain two or more variations of the transepithelial carriers described herein.

The peptide with incretin hormone activity may be delivered transepithelially, either by direct application to skin or other epithelial tissue or application using a plaster or patch material. In some embodiments, the composition containing the peptide with incretin hormone activity and the transepithelial carrier peptide are applied directly to epithelial tissue such as skin. In some embodiments, the peptide with incretin hormone activity and the transepithelial carrier are incorporated into a skin contact base such as a cream, lotion or ointment.

There is no particular limitation imposed on the skin contact base in which the above-described cargo-carrier complex is to be incorporated, insofar as it is brought into contact with the skin and permits transcutaneous administration of the peptide with incretin hormone activity from the skin surface. Specific examples of the base include those constituting a semi-solid or solid preparation such as ointment, gel, emulsion, suspension, cataplasm or plaster or a liquid preparation such as lotion or liniment.

As the ointment base, hydrophobic bases such as oils and fats, waxes and hydrocarbons can be employed usually. Specific examples include mineral bases such as yellow vaseline, white vaseline, paraffin, liquid paraffin, plastibase and silicone and animal or vegetable bases such as beeswax and animal or vegetable oils and fats.

For the gel preparation, hydrogel base such as carboxyvinyl polymer, gel base, fat-free ointment and polyethylene glycol can be used.

Examples of the base for emulsion include water-in-oil type bases such as hydrophilic ointment and vanishing cream, and oil-in-water type bases such as hydrophilic vaseline, purified lanolin, aquahole, oicerin, neocerin, hydrogenated lanolin, cold cream and hydrophilic plastibase.

Examples of the base for suspension include lotion and FAPG base (fatty alcohol-propylene glycol) having fine particles such as stearyl alcohol or cetyl alcohol suspended in propylene glycol, that is, a lyogel base.

Examples of the base for cataplasm include gelatin, carboxymethyl cellulose sodium, methyl cellulose, sodium polyacrylate, kaolin, polyvinyl alcohol, polyvinyl pyrrolidone, glycerin, propylene glycol and water.

A lotion is a preparation having an active ingredient finely and uniformly dispersed in an aqueous liquid and can be classified into suspending lotion and emulsion lotion. Examples of the suspending agent include gum arabic, sodium alginate, carboxymethyl cellulose sodium, methyl cellulose and bentonite. Examples of the emulsifying agent include sodium laurylsulfate, Tweens and Spans.

Liniment can be classified into oily solution type, alcohol solution type, emulsion type and suspension type. To such a liniment, an additive such as water, ethanol, fatty oil, glycerin, soap, emulsifying agent or suspending agent may be added.

The preparation of the present invention can be prepared by a known method. For example, the above-described ointment can be prepared by the ordinary mixing or fusion method. In the mixing method, the preparation is obtained by mixing the active ingredient with a portion of a base, adding the remaining portion to the resulting mixture and mixing them to homogenize the mixture. For mass production, a kneader, roll mill or mixer is employed. In the fusion method, base components are molten in the descending order of a melting component and they are mixed until solidified. For mass production, a mixer or three-roll mill is employed. The dermatologic paste or cataplasm resembles the ointment, but the dermatologic paste contains a comparatively large amount of the active ingredient powder compared with the ointment. The paste is prepared in accordance with the method used for the ointment, but in general, the fusing method is employed. The cataplasm is an external preparation used as a poultice and it contains the active ingredient powder and essential oil ingredient.

In some embodiments of the present invention, it is preferred to employ a plaster in the form of a pressure-sensitive adhesive tape in which a so-called pressure-sensitive adhesive which has adhesion at normal temperature is used as a skin contact base. For ease of handling, a layer of the pressure-sensitive adhesive is formed on one side of a backing material.

The above-described pressure-sensitive adhesive layer is preferably formed of an ordinarily-employed medical pressure-sensitive adhesive with a view to preventing rashes caused by the contact of the adhesive layer with the surface of the skin. Examples thereof include acrylic pressure-sensitive adhesives; natural rubber pressure-sensitive adhesives; synthetic rubber pressure-sensitive adhesives such as synthetic isoprene rubber, polyisobutylene rubber, styrene/butadiene rubber, styrene/isoprene/styrene rubber and styrene/butadiene/styrene rubber; silicone pressure-sensitive adhesives; vinyl ester pressure-sensitive adhesives; and vinyl ether pressure-sensitive adhesives. It is preferred to use, among them, at least one adhesive selected from acrylic, rubber or silicone pressure-sensitive adhesive in consideration of stable quality and easy adjustment of adhesion properties. Particularly, acrylic pressure-sensitive adhesives comprising alkyl acrylate or alkyl methacrylate as the main component are preferred.

As the above-described acrylic pressure-sensitive adhesive, polymers prepared by polymerizing an alkyl (meth)acrylate in a proportion not less than 40% by weight based on the total amount of the monomers to be polymerized are preferred. Copolymers prepared by copolymerizing 50 to 98% by weight of one or more alkyl (meth)acrylates and 2 to 50% by weight of one or more copolymerizable monomers are particularly preferred.

Examples of such an alkyl (meth)acrylate include esters of from a primary to tertiary alcohol having a $C_{2-18}$, preferably $C_{4-12}$, alkyl group and acrylic or methacrylic acid.

Examples of the copolymerizable monomer include monomers each having in its molecule at least one unsaturated double bond which takes part in the copolymerization reaction and in its side chain a functional group such as carboxyl group (for example, (meth)acrylic acid, itaconic acid, maleic acid or maleic anhydride), hydroxyl group (for example, hydroxyethyl (meth)acrylate or hydroxypropyl (meth)acrylate), sulfoxyl group (for example, styrenesulfonic acid, allylsulfonic acid, sulfopropyl (meth)acrylate, (meth)acryloyloxynaphthalenesulfonic acid or acrylamidomethylpropanesulfonic acid), amino group (for example, aminoethyl (meth)acrylate, dimethylaminoethyl (meth)acrylate or tert-butylaminoethyl (meth)acrylate), amide group (for example, (meth)acrylamide, dimethyl (meth)acrylamide, N-butyl acrylamide, N-methylol (meth)acrylamide or N-methylolpropane (meth)acrylamide), or alkoxyl group (for example, methoxyethyl (meth)acrylate, ethoxyethyl (meth)acrylate, methoxyethyleneglycol (meth)acrylate, methoxydiethyleneglycol (meth)acrylate, methoxypolyethyleneglycol (meth)acrylate, methoxypolyethyleneglycol (meth)acrylate or tetrahydrofulfuryl (meth)acrylate).

Examples of the copolymerizable monomer include (meth)acrylonitrile, vinyl acetate, vinyl propionate, N-vinyl-2-pyrrolidone, methyl vinyl pyrrolidone, vinylpyridine, vinyl piperidone, vinyl pyrimidine, vinyl piperazine, vinyl pyrazine, vinyl pyrrole, vinyl imidazole, vinyl caprolactam, vinyl oxazole and vinyl morpholine.

The above-exemplified copolymerizable monomers can be provided for copolymerization either singly or in combination. From the viewpoints of adhesion properties such as adhesion or cohesion or releasability of the peptide with incretin hormone activity or a pharmacologically acceptable salt thereof from the pressure-sensitive adhesive layer, however, it is preferred to carry out copolymerization by using, as an essential ingredient, at least one monomer selected from a carboxyl-containing monomer and a hydroxyl-containing monomer in an amount of 1 to 50% by weight, preferably 3 to 20% by weight and, if necessary, the other monomer exemplified above, for example, a vinyl monomer such as vinyl acetate or N-vinyl-2-pyrrolidone in an amount not greater than 40% by weight, preferably not greater than 30% by weight, each based on the total amount of the monomers to be polymerized.

Specific examples of the acrylic pressure-sensitive adhesive include copolymers of 2-ethylhexyl acrylate and acrylic acid, those of 2-ethylhexylacrylate and hydroxyethyl acrylate, those of 2-ethylhexylacrylate and methyl methacrylate, those of 2-ethylhexylacrylate, 2-methoxyethyl acrylate and vinyl acetate, those of 2-ethylhexyl acrylate and vinyl pyrrolidone, those of 2-ethylhexyl acrylate, methyl methacrylate and 2-methoxyethyl acrylate and those of 2-ethylhexyl acrylate, vinyl pyrrolidone and acrylic acid.

The acrylic pressure-sensitive adhesive which can be used in the present invention generally has a number-average molecular weight of from 10,000 to 100,000 and a weight-average molecular weight of from 100,000 to 2,000,000.

In the transepithelial preparation of the present invention, it is possible to incorporate in the skin contact base at least one organic liquid ingredient selected from the group consisting of glycols, oils and fats, fatty acids, alcohols and fatty acid esters. Such an ingredient is able to bring about advantages such as improvement in skin adhesion or skin penetration of the active ingredient or lowering of skin irritation.

Examples of the glycol include ethylene glycol, diethylene glycol, triethylene glycol, polyethylene glycol, propylene glycol and polypropylene glycol. As polyethylene glycol or polypropylene glycol having a high molecular weight, that having a weight average molecular weight of 200 to 1000 is preferably employed.

Examples of the oil and fat include olive oil, castor oil, squalane, orange oil and mineral oil.

Examples of the fatty acid include $C_{6-20}$ fatty acids such as monocapric acid, oleic acid, caprylic acid, lauric acid, undecylenic acid, isostearic acid and linoleic acid.

Examples of the fatty acid ester include $C_{6-20}$ fatty acid esters such as isopropyl myristate, diethyl sebacate, octyl palmitate, ethyl oleate, diethyl phthalate, diisopropyl adipate, ethyl lactate, propylene glycol fatty acid esters, lauryl nicotinate and laurylpyrrolidone carboxylate.

Examples of the alcohol include $C_{1-20}$ alcohols other than the above-described glycols, such as ethanol, methanol, octyl alcohol, ethoxylated stearyl alcohol, 1,3-butanediol, decyl alcohol, cineol and oleyl alcohol.

It is preferred that the organic liquid ingredient is incorporated in the skin contact base in an amount of from 2 to 50% by weight.

When the preparation of the present invention is used in the form of a plaster having a pressure-sensitive adhesive as the skin contact base, it is possible to improve the transcutaneous penetration of the active ingredient by incorporating one or more of the above-described organic liquid components in the pressure-sensitive adhesive layer. The pressure-sensitive adhesive layer can be plasticized owing to its compatibility with the organic liquid ingredient so that the addition of such an organic liquid ingredient makes it possible to impart the skin with soft feeling upon adhesion to the skin surface. Furthermore, an appropriate cohesive force can be imparted to the pressure-sensitive adhesive layer by crosslinking treatment, whereby the skin irritation when the plaster is peeled and removed after use can be reduced.

The organic liquid ingredient is added to the pressure-sensitive adhesive layer in an amount of 25 to 200 parts by weight, preferably 40 to 180 parts by weight, particularly preferably 60 to 180 parts by weight per 100 parts by weight of the pressure-sensitive adhesive. Too small amount of the organic liquid ingredient does not bring about any advantages. Too large amount, on the other hand, lowers the cohesive force owing to excessive plasticization of the pressure-sensitive adhesive layer, which causes an adhesive residue phenomenon on the skin surface even after the cross-linking treatment, resulting in an increase in the skin irritation upon peeling.

In the present invention, it is possible to add, to the pressure-sensitive adhesive layer, rosin, a rosin derivative, a polyterpene resin, a chroman-indene resin, a petroleum resin or a terpene phenol resin as needed.

The above-described plaster requires a backing material for supporting the pressure-sensitive adhesive layer thereon. Examples of such a backing material include a single film or laminate film of cellulose acetate, ethyl cellulose, polyethylene terephthalate, polyethylene, polypropylene, vinyl acetate-vinyl chloride copolymer, soft polyvinyl chloride, polyurethane, polyvinylidene chloride, ethylene-vinyl acetate copolymer, Surlyn or polytetrafluoroethylene, various metallic foils and metal-deposited films. In addition, woven fabric or nonwoven fabric of fibers made of such a material, cloth and paper can also be employed.

As the backing material, sufficient flexibility and skin following property when the resulting transcutaneous preparation is applied to the skin surface can be used. The thickness of the backing material is generally from 0.5 to 200 µm, preferably from 2 to 100 µm, more preferably 5 to 50 µm.

With a view to improving the sustained releasability of the active ingredient, the transepithelial preparation of the present invention can be-formulated as a sustained-release preparation by using a sustained-release base. Such a preparation can be obtained by incorporating a composition prepared by the ordinary means in a special matrix or can be obtained as a sustained-action preparation in which the composition is adhered to the skin or other epithelial surface through a film such that the release of the active ingredient is controlled by the film. As a film for such a sustained-release transepithelial preparation, a microporous film having an average pore size of 0.1 to 1 µm can be employed. Examples of the material of the microporous film include polypropylene, polyolefin and polytetrafluoroethylene.

A plaster, which is one embodiment of the drug treatment for diabetes of the present invention, can be obtained by adhering a release paper on one side of the pressure-sensitive adhesive layer and a backing layer on the other side. The pressure-sensitive adhesive layer is formed by dissolving the components of the pressure-sensitive adhesive in an appropriate solvent, applying the resulting solution to a backing material or peeling paper and then drying the resulting material or paper to remove the solvent.

In the skin contact base layer, it is possible to incorporate an additive such as antioxidant, pigment, filler, transdermal enhancer, stabilizing agent, drug dissolution aid or drug dissolution suppressing agent as needed in an amount ranging from about 2 to 50 parts by weight per 100 parts by weight of the skin contact base.

As the transdermal penetration enhancer, various compounds can be used, which include a compound that has a function to improve solubility and dispersibility of drugs in the pressure-sensitive adhesive layer, a compound that has a function to improve transcutaneous absorption by improving keratin moisture holding ability, keratin softening ability or keratin permeability (loosening), by acting as a permeation enhancer or pore opening agent or by changing surface conditions of the skin and a compound that has these functions simultaneously, and a compound which is possessed of not only these functions but a drug effect improving function to further increase efficacy of drugs.

These transcutaneous penetration enhancers are exemplified below:
glycols such as diethylene glycol, propylene glycol, and polyethylene glycol as a compound which mainly improves drug solubility;
oils and fats such as olive oil, squalene and lanolin as a compound which mainly improves drug dispersibility;
urea derivatives such as urea and allantoin as a compound which mainly improves moisture holding ability of keratin;
polar solvents such as dimethyldecyl phosphoxide, methyloctyl sulfoxide, dimethyllaurylamide, dodecylpyrrolidone, isosorbitol, dimethylacetamide, dimethyl sulfoxide and dimethylformamide as a compound which mainly improves keratin permeability;
salicylic acid which mainly improves keratin softening ability;
amino acids mainly as a permeability enhancer;
benzyl nicotinate mainly as a pore opening agent;
sodium lauryl sulfate mainly having a function to change surface conditions of the skin; and
salocolum which is jointly used with a drug having excellent transcutaneous absorption.

Also useful are a plasticizer such as diisopropyl adipate, phthalic acid esters and diethyl sebacate, hydrocarbons such as liquid paraffin, various emulsifiers, ethoxidized stearyl alcohol, glycerol monoesters such as oleic acid monoglyceride, caprylic acid monoglyceride and lauric acid monoglyceride, higher fatty acid esters such as glycerol diesters, glycerol triesters or a mixture thereof, isopropyl myristate and octyl palmitate, and higher fatty acids such as oleic acid and caprylic acid.

These transcutaneous penetration enhancers may be used as a mixture of two or more.

Preferred embodiments of the invention disclose the use of oligopeptides to facilitate the transdermal delivery of antidiabetic peptide drugs. In preferred embodiments, peptide oligomers composed primarily of arginine residues are covalently tethered to antidiabetic drugs such as glucagon-like peptide-1 and exendin-4. In some embodiments, arginine-containing oligomers complex with extendin-4 through noncovalent interactions.

EXAMPLE 1

Solid-phase Synthesis of Exendin-4 with an N-terminal Cysteine Residue

The sequence of the peptide is:

```
                                              (SEQ ID NO: 31)
H₂N-CHGEGTFTSD LSKQMEEEAV RLFIEWLKNG GPSSGAPPPS-
CONH₂
```

The synthesis is composed of the following steps: (1) swelling/deprotection of resin; (2) extending the peptide chain; (3) cleavage and (4) purification.

1. Swelling/deprotection of resin. 540 mg of Fmoc-Rink (Fmoc-Rink-linker is also known as 4'-{(R,S)-alpha-[1-(9-Fluorenyl)methoxycarbonylamino]-2,4-dimethoxybenzyl}-phenol)amide resin (0.64 mmole/g substitution, 0.346 mmole scale) was swelled in a reaction vessel with DMF (N,N-dimethylformamide) while a nitrogen gas was bubbled through. DMF was drained after 40 minutes. The Fmoc (9-flurenylmethoxycarbonyl) protecting group on the resin was removed by treating the resin twice with 20% piperidine solution in DMF. Each treatment lasted for 5 minutes. After the deprotection, the resin was thoroughly washed with DMF.

2. Extending the peptide chain. The procedure for incorporation of the first ten residues is different from the rest of the residues. Double coupling was employed for the first ten residues. Each coupling took 30 min. In each coupling, 2 equivalent of Fmoc protected amino acid monomer (0.707 mmole) and 2 equivalent of HOBt (N-Hydroxybenzotriazole) (96 mg, 0.707 mmole) was dissolved in 2 ml of DMF. To the mixture was added 120 microliter of DIC (1,3-diisopropylcarbodiimide). The solution was kept at room temperature for at least 10 minutes for activation before being added to the resin. After the addition of the preactivated amino acids, 120 microliter of DIPEA (diisopropylethylamine) was added. The suspension containing the resin and the preactivated amino acid monomer solution was kept standing at room temperature with a gas of bubbling nitrogen passing through. The pressure of the bubbling gas was adjusted so as to allow the efficient mixing of the resin with the preactivated monomer solution. For the first ten residues, the piperidine deprotection step was performed at the end of the second coupling. For residues beyond the first ten, the activation step includes mixing 4 equivalent of Fmoc protected amino acid monomer (1.414 mmole), 4 equivalent of HOBt (192 mg, 1.414 mmole) in 5 ml of DMF, and adding to the solution 240 microliter of DIC. After the addition of the preactivated amino acids, 240 microliter of DIPEA was added. At the end of each coupling cycle, amino acid solution was drained and the resin was thoroughly washed with DMF. The resin was treated twice with 20% piperidine solution in DMF. Each treatment lasted for 3 minutes. The resin was thoroughly washed after the second piperidine treatment. All reactions were carried out in a reaction vessel with a nitrogen gas bubbled through.

After Cys40 was incorporated, the resin was deprotected and was thoroughly washed with DMF.

3. Cleavage. The resin was thoroughly washed with DMF, DCM (dichloromethane) and methanol and was dried in open air. The resin was then suspended in a cleavage mixture composed of 95:2.5:2.5 TFA (trifluoroacetic acid)/TIS (triisopropylsilane)/water, and was allowed to stand at room temperature for 3 hours. At the end, TFA was removed by rotary evaporation. The resultant residue was dissolved in 20% acetonitrile/water mixture and the clear solution was collected by filtration. The solution was freeze dried.

4. Purification. The crude product was dissolved in water, and was purified by preparation HPLC, using a gradient of 30% acetonitrile in water (0.1% TFA) to 55% acetonitrile in water (0.1% TFA) in 40 minutes. Freeze drying of the combined product fractions yielded 100 mg of purified product.

EXAMPLE 2

Solid-phase Synthesis of Transepithelial Carrier and Cargo Peptides

The sequence of the r7c peptide is:

```
H₂N-RRRRRRRC-CONH₂            (SEQ ID NO:32)
```

The sequence of Ex4-L-R7 is

```
                                              (SEQ ID NO: 45)
NH₂-HGEGTFTSDLSKQMEEEAVRLFIEWLKNGGPSSGAPPPSRRRRRR
R-CONH₂
```

The sequence of Ex4-D-R7 is

```
                           (SEQ ID NO: 45 with all D amino acids)
NH₂-HGEGTFTSDLSKQMEEEAVRLFIEWLKNGGPSSGAPPPS_D R_D R_D R_D
R_D R_D R_D R-CONH₂
```

The sequence of Ex4 is

```
                                              (SEQ ID NO: 6)
NH₂-HGEGTFTSDLSKQMEEEAVRLFIEWLKNGGPSSGAPPPS-CONH₂
```

Syntheses of the transepithelial carrier and cargos follow the same procedure as described in Example 1.

EXAMPLE 3

Activation of the Transepithelial Carrier for Conjugation

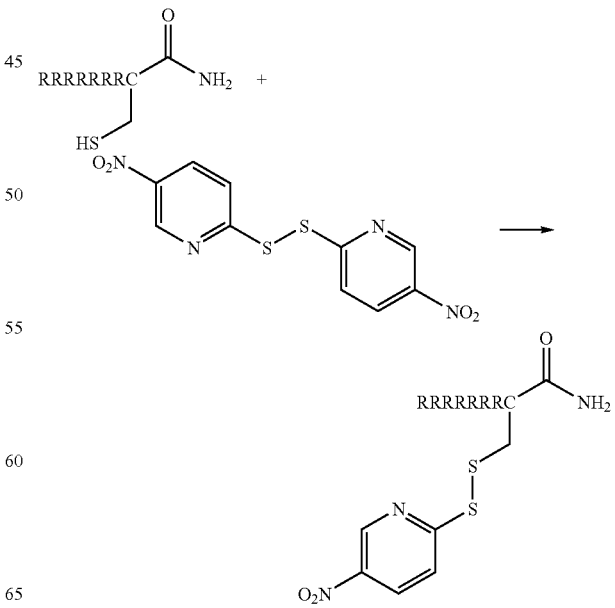

A sample of purified r7c (250 mg, 0.2 mmole) was dissolved in 70 mL of 3:1 acetic acid/water. To this solution, 20 equivalent of dithio-bis(5-nitropyridine) (DTNP) was added. The mixture was stirred at room temperature for 72 hours. The solvent was removed by rotary evaporation at 40° C. The residue was redissolved in water, and the excessive DTNP was removed by washing with ethyl acetate. The aqueous solution was freeze dried to yield 150 mg of product (0.11 mmole, 55%).

EXAMPLE 4

Conjugation of Exendin-4 with Transepithelial Carrier

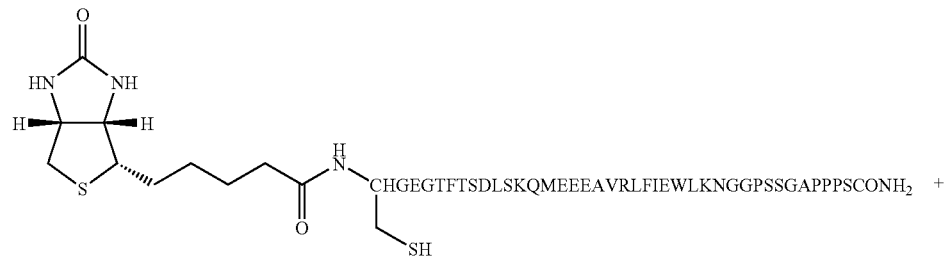

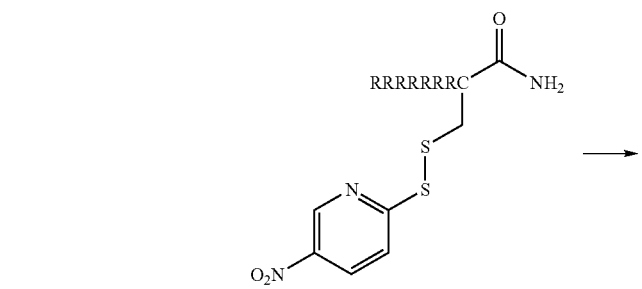

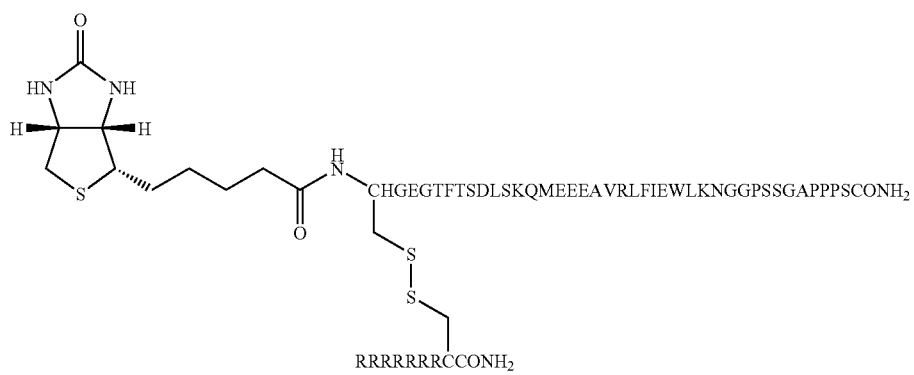

A sample of exendin-4 (25 mg, 5.5 mmole) was dissolved in 2.4 mL of degassed 1M ammonium acetate aqueous solution (pH6). The solution was titrated with a solution of 51 mg of 5-sulfenyl-2-nitropyridine (SNP) linked r7c (see Example 3, 37 mmole) in 15 mL of degassed 0.1% HOAc aqueous solution. The mixture was kept at room temperature (R.T.) overnight. The solvent was removed by freeze drying. The crude product was purified by preparation HPLC to yield 4.0 mg of purified product (0.80 mmole, 15%).

EXAMPLE 5

Incretin Peptide Detection in Mouse: GLP-1 Detection in Nude Mice Skin

TABLE 3

| | GLP-1 TREATMENTS | | |
|---|---|---|---|
| Sample | Concentration of peptide | Volume [μl] | hour |
| A Biotin-GLP-1 | 1 mM | 50 μl in pottasium acetate buffer | 1 or 2 |

TABLE 3-continued

| | GLP-1 TREATMENTS | | |
|---|---|---|---|
| Sample | Concentration of peptide | Volume [μl] | hour |
| B Biotin-R7-GLP-1 | 1 mM | 50 μl in pottasium acetate buffer | 1 or 2 |

TABLE 3-continued

GLP-1 TREATMENTS

| Sample | | Concentration of peptide | Volume [µl] | hour |
|---|---|---|---|---|
| C | Biotin-TAT-GLP-1 | 1 mM | 50 µl in pottasium acetate buffer | 1 or 2 |
| D | Biotin-Cys-GLP-1/R7-Cys | 1 mM | 50 µl in pottasium acetate buffer | 1 or 2 |
| E | Biotin-Cys-GLP-1/TAT-Cys | 1 mM | 50 µl in pottasium acetate buffer | 1 or 2 |
| F | Biotin-GLP-1 | 1 mM | 50 µl in pottasium acetate buffer | 1 or 2 |
| G | (no treatment) | — | 50 µl in pottasium acetate buffer | 1 or 2 |

The mouse skins were treated with the GLP-1 peptide prepared as described above (Table 3). The mice were injected with an anesthesia and the peptide solution was applied to the mouse skin (see FIG. 1). After 1-2 hours, the treated mice were sacrificed and the treated skin was removed. The treated skins were quickly frozen in liquid nitrogen, and embedded in polymer. Sections (5-6 µm thick) were mounted onto glass slides. Visualization of the peptides was performed by the following immunohistochemical method.

Figure 1C:
FIG. 1 shows immunohistological detection of GLP1 cargo peptide with visualization by green fluorescent signal (FITC) after R7 mediated transdermal administration. Panel A Biotin-SH-GLP1 (no PTD carrier), Panel B shows the R7 mediated GLP1 with disulfide bridge conjugation on peptide transdermal delivery and Panel C shows the Tat peptide medicated GLP1 with disulfide bridge conjugation on peptide transdermal delivery.
Figure 1B:
Figure 1A:
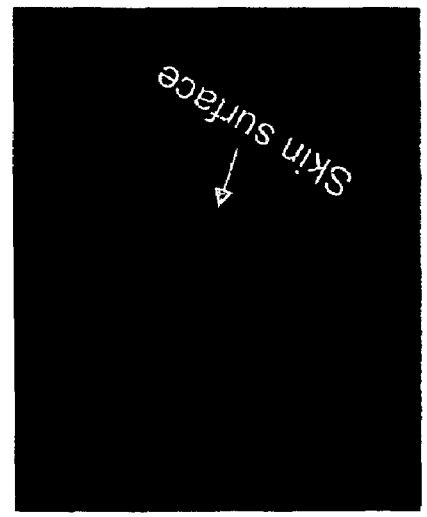

The sliced sections were fixed in 100% acetone and blocked with 4% BSA/0.1% triton X-100 in PBS for 1 hour at room temperature. The sections were incubated with 40 µg/ml of goat anti-GLP-1 polyclonal antibody (Goat anti-GLP-1(C-17) IgG, Santa Cruz Biotechnology, Inc., 200 µg/ml) in 4% BSA-PBS solution at 4° C. overnight. The sections were washed 3 times in PBS for 5 min. Next, the sections were incubated with FITC labeled rabbit anti-goat IgG (FITC-conjugated AffiniPure Rabbit Anti-Goat IgG(H+L), 305-095-003, Jackson ImmunoResearch LABORATORIES, INC.) at a dilution of 1:100 with PBS for 1 hour at room temperature. The sections were washed 3 times in PBS for 5 min., and were removed gently from solution (don't dry completely). The sections were mounted using Cytoseal 60 (Electron Microscopy Science). The immunoreactions were then observed under an Axioscope microscope. FIG. 1 shows skin penetration with samples D and E.

TABLE 4

EXENDIN-4 (EX-4) DETECTION IN DIABETIC MOUSE SKIN Samples

| Group | Application route | Sample | Application amount | trial |
|---|---|---|---|---|
| J | transdermal | 50 mM Exendin-4-(D)R7 in PBS | 10 uL | N = 3 |
| K | 120 min | 50 mM Exendin-4-(L)R7 in PBS | 10 uL | N = 3 |
| L | | PBS | 10 uL | N = 3 |

Applied area: 15 mm × 15 mm in Group J, K, L. 40 mm × 40 mm in Group M, N
Diabetic mice: BLS.C g - + Lepr$^{db}$/Lepr$^{db}$/Jc1, Japan CLEA, female, 13-14 weeks After an overnight fast, blood (about 3 uL) was taken from tail vein, and the initial blood glucose level (0 min) was checked using Savon Test strip. Some blood was centrifuged to get serum. A test sample (10 uL or 40 uL) sample was applied on the back skin of the mice and incubated for 120 minutes. (By the end of the incubation period, the sample was dried up.)

Glucose was orally administered (Glucose conc.: 250 mg/mL PBS, amount: 4 mL/kg). 30, 60, 120, 240 min after glucose was orally administered, blood (about 30 uL ) was taken from tail vein and the blood glucose level was checked using Savon Test strip. Some blood was centrifuged to get serum.

Skin was taken for cut section study.

Serum(0, 30, 120 min) was stored in −40 degree until the measurement of blood insulin level. Insulin level was measured by ELISA kit (Mercodia Ultrasensitive Mouse Insulin ELISA).

Immunohistochemistry (by Rabbit Anti-Ex-4 Polyclonal Antibody)

15 um thick skin cryosections were prepared. The cryosections were adhered to Silane-coated slides (DAKO, No.S3003) for 30 min at room temperature (RT). The slides were fixed in acetone for 10 minutes at 4° C. followed by washing in PBS for 10 min at RT.

The slides were incubated in 3% hydrogen peroxide in PBS for 10 minutes at RT to quench endogenous peroxidase activity followed by washing with three changes of PBS for 5 min each.

For immunostaining of tissue sections, "ABC high-HRP Immunostaining Kit" (TOYOBO, No.ISK-201) was used. All steps were carried out at room temperature in a humidified chamber. The sections were incubated for 1 hour in "Blocking Reagent" (Normal goat serum in PBS). The Blocking Reagent was removed followed by incubation with primary antibody (HOKUDOH, rabbit anti-Ex-4 polyclonal antibody, 40 ug/ml in "Blocking Reagent") for 30 min. The sections were washed with three changes of PBS for 5 min each.

The sections were incubated for 30 min with "Biotin-conjugated secondary antibody" followed by washing with three changes of PBS for 5 min each.

The sections were incubated for 30 min with "Avidin-biotinylated peroxidase complex reagent" followed by washing with three changes of PBS for 5 min each.

The sections were incubated in "Peroxidase substrate" (TMB: 3,3',5,5'-tetramethylbenzidine) for 7 min. followed by washing in deionized water twice for 1 min each.

Excess water was wiped off and 1 drop of aqueous permanent mounting medium (DAKO, No.S1964) was immediately added, covered with a coverslip and observed by light microscopy (×100).

Figure 2:
FIG. 2 shows mmunohistological detection of Ex-4 cargo peptide with visualization by HRP-TMB Staining after R7 mediated transdermal administration. Panel A shows the background signal; Panel B shows the evidence of Ex-4-D-

The results showed that Ex4 can be successfully delivered through skin with the help of R7 (D or L) (FIG. 2).

EXAMPLE 6

Blood Glucose Detection

The peptides of Example 4 were prepared for treatment of the nude mice. A solution of 1 mM peptide was prepared by dilution with 0.2 M potassium acetate (pH 3.8). The mice were injected with anesthesia. The back of the mice was wiped with 0.9% NaCl or alcohol. 30 µl of the peptide solution was applied to the back of the mice and dried.

Alternatively, 100 µl of the peptide solution was applied to the cloth of the patch. The patch was applied to the back of the mouse and left on the mouse overnight. A new patch containing 100 µl of the peptide solution was applied to the mouse's back each day during the glucose detection testing.

The glucose detection was carried out as follows. Anesthesia was injected into the test animal. Blood was withdrawn from the tail vein for detection of the glucose level. Glucose (31 mg/50 µl d.w.) was injected into the tail vein at time 0.

Before 3 minutes, cut the tail and take blood at 3, 6, 10, 20, 30, and 50 min. after the glucose challenge. The glucose level was detected with a glucose detection kit. After finishing the glucose detection, whole blood was taken from the heart, and the treated skin was removed. The removed skin was put on a disposable small dish, and frozen with liquid nitrogen immediately. Blood samples were centrifuged at 5000 rpm for 5-10 min., the supernatant was collected and stored in the freezer.

When the formulation which composed R7-s-s-Ex4, R7-s-s-R7 and C-Ex4 applied on the skin of nude mice, these compositions increase the glucose recovery rate in the mice after tail vein-administered glucose challenge (FIG. 3).

EXAMPLE 7

In Vitro Human Skin Flux Study Protocol

An in vitro flux study was done using human skin which contained epidermis and stratum corneum. Saline containing 0.01% $NaN_3$ was used as receptor solution. Human skin was set on the cell. The diameter of the effective area of the skin was 3/8 inch. and the area was 0.11 square inch. Test sample solution (200 uL) was loaded onto the skin. The receptor solution was kept stirring and the cells were kept in 32° C. during flux study. At 6, 22, 30, and 48 hour time points, receptor solution was collected for analysis. At 6, 22, and 30 hour time points, another saline containing 0.010% $NaN_3$ was added into the receptor cell after sampling. Collected receptor solution was condensed by freeze drying, redissolved in 300 uL of solvent (5% acetonitrile, 0.1%TFA), and analyzed by HPLC. Conditions of the HPLC are described below.
HPLC condition
  Mobile phase (Gradient)
    B %: 5%15 min→95%→3 min→95%→2 min→5%→7 min→5%
    B %: 5%→95% (15 min.)
    B %: 95% (3 min.)
    B %: 95%-5% (2 min.)
    B %: 5% (7 min.)
    Solvent A: 0.1%TFA in water, Solvent B: 0.1%TFA in acetonitrile
  Flow rate: 1 mL/min, column temperature: room temperature,
  Injection volume: 250 uL, Detector: photodiode-array (280 nm)
  Column: Waters Symmetry $C_{18}$ 5 um 100A, 4.6×150 mm

TABLE 3

Samples of the penetration study

| | C-Ex4-Bio | R7C | R7C dimer |
|---|---|---|---|
| Group 1 (C-Exendin4-Biotin) | 2.56 mg/mL (0.57 mM) | | |
| Group 2: mixture (C-Exendin4-Biotin & R7C) | 2.56 mg/mL (0.57 mM) | 3.04 mg/mL (2.5 mM) | |
| Group 3: mixture (C-Exendin4-Biotin & R7Cdimer) | 2.56 mg/mL (0.57 mM) | | 3.04 mg/mL (1.25 mM) |
| Group 4 (Blank: Water) | | | |

Loading amount: 200 uL on each skin

These preferred compositions (Group 2 and Group 3) penetrated stratum corneum from human skin tissues (FIG. 4).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A topical preparation for the treatment of diabetes comprising: a conjugate comprising a peptide with incretin hormone activity covalently attached to a transepithelial carrier; and
   a skin contact base,
   wherein the conjugate has a concentration in the skin contact base from 0.001% to 70%,
   wherein the peptide with incretin hormone activity is SEQ ID NO:6 or SEQ ID NO:33 optionally having a cysteine amino acid residue attached to the N-terminus or the C-terminus of the peptide with incretin activity, or having a cysteine amino acid residue which replaces one of the serine amino acid residues in the peptide with incretin activity, and
   wherein the transepithelial carrier comprises SEQ ID NO:32.

2. The topical preparation of claim 1, wherein the topical preparation is a conjugate selected from the group consisting of structures (V) and (VI) as follows:

wherein:
   Q comprises the transepithelial carrier;
   L comprises the peptide;
   X is a linkage formed between a functional group on the peptide and a functional group on the carrier;
   T is a small oligopeptide linker;
   Y is a linkage formed between a functional group on the linker and a functional group on the carrier;

Z is a linkage formed between a functional group on the peptide and a functional group on the linker;

wherein X, Y and Z are independently selected from the group consisting of —S—S—, —C(=O)O—, C(=O)S—, —C(=O)NH—, —C(=S)NH—, —OC(=O)NH—, —NHC(=O)NH—, an acetal linkage, a semi-acetal linkage, —SONH—, —SO$_2$NH—, and —CA=N—, wherein A is selected from the group consisting of H, alkyl and aryl;

m is an integer from 1-5.

3. The topical preparation of claim 2, wherein structures V and VI are capable of degradation by hydrolysis or glutathione-assisted reduction to release the peptide with incretin hormone activity in its bioactive form.

4. The topical preparation of claim 1, wherein at least one amino acid in the transepithelial carrier is a D-amino acid.

5. The topical preparation of claim 1, wherein all of the amino acids in the transepithelial carrier are D-amino acids.

6. The topical preparation of claim 1, wherein the peptide with incretin activity comprises at least one cysteine amino acid residue, wherein the at least one cysteine is introduced by addition or replacement.

7. The topical preparation of claim 6, wherein at least one amino acid in the transepithelial carrier is a D-amino acid.

8. The topical preparation of claim 6, wherein all of the amino acids in the transepithelial carrier are D-amino acids.

9. The topical preparation of claim 1 wherein the peptide with incretin hormone activity is targeting glucagon-like peptide-1 receptors and glucose-dependent insulinotropic polypeptide receptors.

10. The topical preparation of claim 1, wherein the skin contact base is selected from the group consisting of an ointment, a gel, an emulsion, a suspension, a cataplasm, a plaster, a lotion and a liniment.

11. The topical preparation of claim 1, wherein the skin contact base is a plaster, comprising a pressure sensitive adhesive and a backing.

12. The topical preparation of claim 11, further comprising water or an organic liquid ingredient, which is added to the pressure sensitive adhesive layer.

13. The topical preparation of claim 12, wherein the organic liquid ingredient is selected from the group consisting of glycol, olive oil, castor oil, squalane, orange oil, mineral oil, $C_{6-20}$ fatty acid, $C_{6-20}$ fatty acid ester and $C_{1-20}$ alcohol.

14. The topical preparation of claim 1, wherein the skin contact base provides sustained release.

15. The topical preparation of claim 1, wherein the epithelial tissue is skin tissue.

16. A method of treating type 2 diabetes in a human subject in need thereof, comprising administering the topical preparation of claim 1 to the human subject.

17. A method for treating type 2 diabetes in a human subject in need thereof, the method comprising:

providing a topical preparation comprising a peptide with incretin hormone activity and a transepithelial carrier according to claim 1;

placing said topical preparation in contact with the skin of a patient such that said active agent is released topically onto said skin of said patient such that said peptide with incretin hormone activity is released onto said skin of said patient; and delivering an effective dose of the peptide with incretin hormone activity to stimulate the secretion of insulin in vivo in the human subject in need thereof, without inducing serious nausea and/or vomiting.

18. The method of claim 17 wherein the peptide with incretin hormone activity is targeting glucagon-like peptide-1 receptors and glucose-dependent insulinotropic polypeptide receptors.

19. A topical preparation for the treatment of diabetes comprising:

a peptide comprising SEQ ID NO: 45; and a skin contact base, wherein the peptide has a concentration in the skin contact base from 0.001% to 70%.

20. The topical preparation of claim 19, wherein at least one amino acid in the peptide is a D-amino acid.

21. The topical preparation of claim 19, wherein all of the amino acids in the peptide are D-amino acids.

22. The topical preparation of claim 19, wherein the skin contact base is selected from the group consisting of an ointment, a gel, an emulsion, a suspension, a cataplasm, a plaster, a lotion and a liniment.

23. The topical preparation of claim 19, wherein the skin contact base is a plaster, comprising a pressure sensitive adhesive and a backing.

24. The topical preparation of claim 23, further comprising water or an organic liquid ingredient, which is added to the pressure sensitive adhesive layer.

25. The topical preparation of claim 24, wherein the organic liquid ingredient is selected from the group consisting of glycol, olive oil, castor oil, squalane, orange oil, mineral oil, $C_{6-20}$ fatty acid, $C_{6-20}$ fatty acid ester and $C_{1-20}$ alcohol.

26. The topical preparation of claim 19, wherein the skin contact base provides sustained release.

27. The topical preparation of claim 19, wherein the epithelial tissue is skin tissue.

28. A method of treating type 2 diabetes in a human subject in need thereof, comprising administering the topical preparation of claim 19 to the human subject.

29. A method for treating type 2 diabetes in a human subject in need thereof, the method comprising:

providing a topical preparation comprising a peptide with incretin hormone activity and a transepithelial carrier according to claim 19;

placing said topical preparation in contact with the skin of a patient such that said peptide with incretin hormone activity is released topically onto said skin of said patient; and delivering an effective dose of the peptide with incretin hormone activity to stimulate the secretion of insulin in vivo in the human subject in need thereof, without inducing serious nausea and/or vomiting.

* * * * *

UNITED STATES PATENT AND TRADEMARK OFFICE
CERTIFICATE OF CORRECTION

PATENT NO.         : 7,442,682 B2
APPLICATION NO. : 11/219145
DATED                  : October 28, 2008
INVENTOR(S)       : Kitaura et al.

It is certified that error appears in the above-identified patent and that said Letters Patent is hereby corrected as shown below:

Title Page 1, Column 2, Line 3, "Daibetes, Heart Disease" should be changed to

--Diabetes, Heart Disease--

Column 2, Line 57, "of β cells to GIP." should be changed to --of β-cells to GIP.--

Column 9, Line 34, "—CH2NR—, — CH2CH2C" should be changed to

-- —$CH_2NR$—, —$CH_2CH_2C$--

Column 9, Line 35, "CH2—, —SOCH2—" should be changed to --$CH_2$—, —$SOCH_2$— --

Column 9, Line 36, "—CH2OC" should be changed to -- —$CH_2OC$--

Column 9, Line 49, "In preferred embodments," should be changed to --In preferred embodiments--

Column 10, Line 24, "any of the the" should be changed to --any of the--

Column 14, Line 1, "—CH2NR—, —CH2CH2C" should be changed to

-- —$CH_2NR$—, —$CH_2CH_2C$--

Column 14, Line 2, "—CH2—, —SOCH2—" should be changed to

-- —$CH_2$—, —$SOCH_2$— --

Column 14, Line 3, "—CH2OC" should be changed to -- —$CH_2OC$--

Column 14, Line 16, "In preferred embodments," should be changed to --In preferred embodiments--

Column 14, Line 64, "shows mmunohistological" should be changed to --shows immunohistological--

UNITED STATES PATENT AND TRADEMARK OFFICE
CERTIFICATE OF CORRECTION

PATENT NO. : 7,442,682 B2
APPLICATION NO. : 11/219145
DATED : October 28, 2008
INVENTOR(S) : Kitaura et al.

It is certified that error appears in the above-identified patent and that said Letters Patent is hereby corrected as shown below:

Column 18, Line 54, "with incertin hormone" should be changed to --with incretin hormone--

Column 19, Line 28, "flumaric acid and" should be changed to --fumaric acid and--

Column 23, Line 2, "of the formula (IV)," should be changed to --of the formula (IV):--

Column 27, Line 63, "—C(═O)—," should be changed to -- —C(═O)S—,--

Column 27, Line 64, "—(═O)NH—," should be changed to -- —C(═O)NH—,--

Column 28, Line 61, "sodium laurylsulfate," should be changed to --sodium lauryl sulfate,--

Column 30, Line 7, "or tetrahydrofulfuryl(meth)acrylate)." should be changed to --or tetrahydrofurfuryl(meth)acrylate).--

Column 30, Lines 24-25, "exemplifed above," should be changed to --exemplified above,--

Column 33, Line 18, "phenol)amide resin" should be changed to --phenol) amide resin--

Column 36, Line 12, "50 µl in pottasium" should be changed to --50 µl in potassium--

Column 36, Line 65, "50 µl in pottasium" should be changed to --50 µl in potassium--

Column 37, Line 7, "50 µl in pottasium" should be changed to --50 µl in potassium--

Column 37, Line 9, "50 µl in pottasium" should be changed to --50 µl in potassium--

Column 37, Line 11, "50 µl in pottasium" should be changed to --50 µl in potassium--

Column 37, Line 13, "50 µl in pottasium" should be changed to --50 µl in potassium--

UNITED STATES PATENT AND TRADEMARK OFFICE
CERTIFICATE OF CORRECTION

PATENT NO. : 7,442,682 B2
APPLICATION NO. : 11/219145
DATED : October 28, 2008
INVENTOR(S) : Kitaura et al.

It is certified that error appears in the above-identified patent and that said Letters Patent is hereby corrected as shown below:

Column 37, Line 15, "50 µl in pottasium" should be changed to --50 µl in potassium--

Column 37, Line 61, "(about 3 uL) was" should be changed to --(about 30 uL) was--

Column 38, Line 15, "15 um thick skin" should be changed to --15 µm thick skin--

Column 40, Line 3, "B %: 95%-5% (2 min.)" should be changed to

--B %: 95%→5% (2 min.)--

Column 40, Line 11, "5 um 100 A," should be changed to --5 µm 100 A,--

Column 60, Lines 54-56, "(V)

(VI)" should be changed to --(V)
                                and
                              (VI)--

Signed and Sealed this

Thirty-first Day of March, 2009

JOHN DOLL
*Acting Director of the United States Patent and Trademark Office*

SEQUENCE LISTING

<160> NUMBER OF SEQ ID NOS: 45

<210> SEQ ID NO 1
<211> LENGTH: 204
<212> TYPE: PRT
<213> ORGANISM: Heloderma suspectum

<400> SEQUENCE: 1

Met Thr Ser Met Tyr Phe Val Ala Gly Leu Leu Leu Met Ile Val Gln
1               5                   10                  15

Gly Ser Trp Gln Ser Pro Leu Gln Glu Thr Glu Glu Lys Ser Arg Ser
            20                  25                  30

Phe Lys Ala Ser Gln Ala Glu Pro Leu Asp Asp Ser Arg Gln Leu Asn
        35                  40                  45

Glu Val Lys Arg His Ser Gln Gly Thr Phe Thr Ser Asp Tyr Ser Lys
    50                  55                  60

Tyr Leu Asp Thr Arg Arg Ala Gln Asp Phe Val Gln Trp Leu Met Asn
65                  70                  75                  80

Thr Lys Arg Ser Gly Gln Gln Gly Val Glu Glu Arg Glu Lys Glu Asn
                85                  90                  95

Leu Leu Asp Gln Leu Ser Ser Asn Gly Leu Ala Arg His His Ala Glu
            100                 105                 110

Tyr Glu Arg His Ala Asp Gly Arg Tyr Thr Ser Asp Ile Ser Ser Tyr

```
                    115                 120                 125
Leu Glu Gly Gln Ala Ala Lys Glu Phe Ile Ala Trp Leu Val Asn Gly
    130                 135                 140

Arg Gly Arg Arg Asp Phe Leu Glu Glu Ala Gly Thr Ala Asp Asp Ile
145                 150                 155                 160

Gly Arg Arg His Ala Asp Gly Thr Phe Thr Ser Asp Tyr Asn Gln Leu
                165                 170                 175

Leu Asp Asp Ile Ala Thr Gln Glu Phe Leu Lys Trp Leu Ile Asn Gln
            180                 185                 190

Lys Val Thr Gln Arg Asp Leu Leu Gly Glu Tyr Gln
        195                 200

<210> SEQ ID NO 2
<211> LENGTH: 87
<212> TYPE: PRT
<213> ORGANISM: Heloderma suspectum

<400> SEQUENCE: 2

Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu Glu
    50                  55                  60

Ala Val Arg Leu Phe Ile Glu Trp Leu Lys Asn Gly Gly Pro Ser Ser
65                  70                  75                  80

Gly Ala Pro Pro Pro Ser Gly
                85

<210> SEQ ID NO 3
<211> LENGTH: 39
<212> TYPE: PRT
<213> ORGANISM: Heloderma horridum

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 35
<212> TYPE: PRT
<213> ORGANISM: Heloderma suspectum

<400> SEQUENCE: 4

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 5
```

```
<211> LENGTH: 38
<212> TYPE: PRT
<213> ORGANISM: Heloderma suspectum

<400> SEQUENCE: 5

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 6
<211> LENGTH: 39
<212> TYPE: PRT
<213> ORGANISM: Artificial Sequence
<220> FEATURE:
<223> OTHER INFORMATION: chemically synthesized exendin-4
<220> FEATURE:
<221> NAME/KEY: AMIDATION
<222> LOCATION: (39)...(39)

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 7
<211> LENGTH: 30
<212> TYPE: PRT
<213> ORGANISM: Homo sapiens

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Exendin or GLP-1 agonist

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 9
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 9

His Gly Glu Gly Thr Phe Thr Ser Asp Leu Ser Lys Gln Met Glu Glu
1               5                   10                  15
```

-continued

Glu Ala Val Arg Leu Phe Ile Glu Trp Leu Lys Asn
            20                  25

<210> SEQ ID NO 10
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 10

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 11

His Ala Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 12

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 13

His Gly Glu Gly Thr Ala Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 14
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 14

His Gly Glu Gly Thr Phe Thr Ala Asp Leu Ser Lys Gln Leu Glu Glu

```
                1               5                  10                  15
Glu Ala Val Arg Leu Phe Ile Glu Phe Leu Lys Asn
            20                  25

<210> SEQ ID NO 15
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 15

His Gly Glu Gly Thr Phe Thr Ser Asp Ala Ser Lys Gln Leu Glu Glu
  1               5                  10                  15

Glu Ala Val Arg Leu Phe Ile Glu Phe Leu Lys Asn
            20                  25

<210> SEQ ID NO 16
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 16

His Gly Glu Gly Thr Phe Thr Ser Asp Leu Ala Lys Gln Leu Glu Glu
  1               5                  10                  15

Glu Ala Val Arg Leu Phe Ile Glu Phe Leu Lys Asn
            20                  25

<210> SEQ ID NO 17
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 17

His Gly Glu Gly Thr Phe Thr Ser Asp Leu Ser Lys Ala Leu Glu Glu
  1               5                  10                  15

Glu Ala Val Arg Leu Phe Ile Glu Phe Leu Lys Asn
            20                  25

<210> SEQ ID NO 18
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 18

His Gly Glu Gly Thr Phe Thr Ser Asp Leu Ser Lys Gln Ala Glu Glu
  1               5                  10                  15

Glu Ala Val Arg Leu Phe Ile Glu Phe Leu Lys Asn
            20                  25

<210> SEQ ID NO 19
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 19
```

His Gly Glu Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 20
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 20

His Gly Glu Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 21
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 21

His Gly Glu Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 22
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 22

His Gly Glu Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 23

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 24
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 24

His Gly Glu Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 25

His Gly Glu Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 26
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 26

His Gly Glu Gly Thr Phe Thr Ser Asp Leu Ser Lys Gln Leu Glu Glu
1               5                   10                  15

Glu Ala Val Arg Leu Phe Ile Ala Phe Leu Lys Asn
            20                  25

<210> SEQ ID NO 27
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 27

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 28
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 28

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: Exendin or GLP-1 agonist

```
<400> SEQUENCE: 29

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: Exendin or GLP-1 agonist

<400> SEQUENCE: 30

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 31
<211> LENGTH: 40
<212> TYPE: PRT
<213> ORGANISM: Artificial Sequence
<220> FEATURE:
<223> OTHER INFORMATION: Exendin-4 mofified with cysteine at N-terminus
<220> FEATURE:
<221> NAME/KEY: AMIDATION
<222> LOCATION: (40)...(0)

<400> SEQUENCE: 31

Cys His Gly Glu Gly Thr Phe Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40

<210> SEQ ID NO 32
<211> LENGTH: 8
<212> TYPE: PRT
<213> ORGANISM: Artificial Sequence
<220> FEATURE:
<223> OTHER INFORMATION: Artificial peptide for transdermal transport
<220> FEATURE:
<221> NAME/KEY: AMIDATION
<222> LOCATION: (8)...(0)

<400> SEQUENCE: 32

Arg Arg Arg Arg Arg Arg Arg Cys
1               5

<210> SEQ ID NO 33
<211> LENGTH: 40
<212> TYPE: PRT
<213> ORGANISM: Artificial Sequence
<220> FEATURE:
<223> OTHER INFORMATION: Exendin peptide

<400> SEQUENCE: 33

His Ser Asp Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40
```

```
<210> SEQ ID NO 34
<211> LENGTH: 153
<212> TYPE: PRT
<213> ORGANISM: Homo sapiens
<220> FEATURE:
<221> NAME/KEY: PEPTIDE
<222> LOCATION: (0)...(0)
<223> OTHER INFORMATION: glucose-dependent insulinotropic polypeptide

<400> SEQUENCE: 34

Met Val Ala Thr Lys Thr Phe Ala Leu Leu Leu Ser Leu Phe Leu
 1               5                  10                  15

Ala Val Gly Leu Gly Glu Lys Lys Glu Gly His Phe Ser Ala Leu Pro
            20                  25                  30

Ser Leu Pro Val Gly Ser His Ala Lys Val Ser Ser Pro Gln Pro Arg
        35                  40                  45

Gly Pro Arg Tyr Ala Glu Gly Thr Phe Ile Ser Asp Tyr Ser Ile Ala
    50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
        115                 120                 125

Leu Arg Asp Leu Leu Ile Gln Glu Leu Leu Ala Cys Leu Leu Asp Gln
    130                 135                 140

Thr Asn Leu Cys Arg Leu Arg Ser Arg
145                 150

<210> SEQ ID NO 35
<211> LENGTH: 45
<212> TYPE: PRT
<213> ORGANISM: Artificial Sequence
<220> FEATURE:
<223> OTHER INFORMATION: GLP-1 receptor agonist (ZP10A)

<400> SEQUENCE: 35

His His Gly Glu Gly Thr Phe Thr Ser Asp Leu Ser Lys Gln Met Glu
 1               5                  10                  15

Glu Glu Ala Val Arg Leu Phe Ile Glu Trp Leu Lys Asn Gly Gly Pro
            20                  25                  30

Ser Ser Gly Ala Pro Pro Ser Lys Lys Lys Lys Lys Lys
        35                  40                  45

<210> SEQ ID NO 36
<211> LENGTH: 16
<212> TYPE: PRT
<213> ORGANISM: Artificial Sequence
<220> FEATURE:
<223> OTHER INFORMATION: pAntp(43-58); penetratin; protein transduction
      domain

<400> SEQUENCE: 36

Arg Gln Ile Lys Ile Trp Phe Gln Asn Arg Arg Met Lys Trp Lys Lys
 1               5                  10                  15

<210> SEQ ID NO 37
```

```
<211> LENGTH: 16
<212> TYPE: PRT
<213> ORGANISM: Artificial Sequence
<220> FEATURE:
<223> OTHER INFORMATION: retro- inverso pAntp(43-58); protein
      transduction domain; all D amino acids

<400> SEQUENCE: 37

Lys Lys Trp Lys Met Arg Arg Asn Gln Phe Trp Val Lys Val Gln Arg
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: W/R penetratin;  protein transduction domain

<400> SEQUENCE: 38

Arg Arg Trp Arg Arg Trp Trp Arg Arg Trp Trp Arg Arg Trp Arg Arg
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: pAntp(52-58); protein transduction domain

<400> SEQUENCE: 39

Arg Arg Met Lys Trp Lys Lys
1               5

<210> SEQ ID NO 40
<211> LENGTH: 9
<212> TYPE: PRT
<213> ORGANISM: Artificial Sequence
<220> FEATURE:
<223> OTHER INFORMATION: HIV tat(49-57);  protein transduction domain

<400> SEQUENCE: 40

Arg Lys Lys Arg Arg Gln Arg Arg Arg
1               5

<210> SEQ ID NO 41
<211> LENGTH: 13
<212> TYPE: PRT
<213> ORGANISM: Artificial Sequence
<220> FEATURE:
<223> OTHER INFORMATION: HIV tat(48-60);  protein transduction domain

<400> SEQUENCE: 41

Gly Arg Lys Lys Arg Arg Gln Arg Arg Arg Pro Pro Gln
1               5                   10

<210> SEQ ID NO 42
<211> LENGTH: 11
<212> TYPE: PRT
<213> ORGANISM: Artificial Sequence
<220> FEATURE:
<223> OTHER INFORMATION: HIV tat(47-57);  protein transduction domain

<400> SEQUENCE: 42

Tyr Gly Arg Lys Lys Arg Arg Gln Arg Arg Arg
1               5                   10

<210> SEQ ID NO 43
```

```
-continued

<211> LENGTH: 7
<212> TYPE: PRT
<213> ORGANISM: Artificial Sequence
<220> FEATURE:
<223> OTHER INFORMATION: r7;All D amino acids; protein transduction
      domain

<400> SEQUENCE: 43

Arg Arg Arg Arg Arg Arg Arg
 1               5

<210> SEQ ID NO 44
<211> LENGTH: 9
<212> TYPE: PRT
<213> ORGANISM: Artificial Sequence
<220> FEATURE:
<223> OTHER INFORMATION: r9; All D amino acids; protein transduction
      domain

<400> SEQUENCE: 44

Arg Arg Arg Arg Arg Arg Arg Arg Arg
 1               5

<210> SEQ ID NO 45
<211> LENGTH: 46
<212> TYPE: PRT
<213> ORGANISM: Artificial Sequence
<220> FEATURE:
<223> OTHER INFORMATION: Chemically synthesized exendin-4 peptide
      covalently linked to arg-7 carrier
<220> FEATURE:
<221> NAME/KEY: AMIDATION
<222> LOCATION: (46)...(46)

<400> SEQUENCE: 45

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser Arg Arg Arg Arg Arg Arg Arg
         35                  40                  45
```